United States Patent
Tucker et al.

(10) Patent No.: US 11,133,094 B2
(45) Date of Patent: Sep. 28, 2021

(54) SYSTEMS AND METHODS FOR VISUALIZING DATA

(71) Applicant: Flatiron Health, Inc., New York, NY (US)

(72) Inventors: Melisa Tucker, Brooklyn, NY (US); Shannon Lee, New York, NY (US); Nathan Nussbaum, South Orange, NJ (US); Dina Levy-Lambert, New York, NY (US)

(73) Assignee: FLATIRON HEALTH, INC., New York, NY (US)

( * ) Notice: Subject to any disclaimer, the term of this patent is extended or adjusted under 35 U.S.C. 154(b) by 0 days.

(21) Appl. No.: 15/717,677

(22) Filed: Sep. 27, 2017

(65) Prior Publication Data

US 2018/0089376 A1    Mar. 29, 2018

Related U.S. Application Data

(60) Provisional application No. 62/401,138, filed on Sep. 28, 2016.

(51) Int. Cl.
*G16H 10/65* (2018.01)
*G16H 40/63* (2018.01)
(Continued)

(52) U.S. Cl.
CPC ........... *G16H 10/65* (2018.01); *G06F 16/248* (2019.01); *G06F 16/9535* (2019.01); *G16H 40/63* (2018.01)

(58) Field of Classification Search
CPC .... G06F 19/328; G06F 19/321; G06F 19/322; G16H 40/63; G16H 10/20; G16H 50/20;
(Continued)

(56) References Cited

U.S. PATENT DOCUMENTS

| 7,895,527 B2 * | 2/2011 | Zaleski | G16H 40/63 715/804 |
| 2004/0153440 A1 * | 8/2004 | Halevy | G06F 16/2471 |

(Continued)

OTHER PUBLICATIONS

Muhammad Sheraz Arshad Malik, Towards the Development of an Interface model for Information visualization in multiple electronic health records, IEEE Xplore, IEEE Conference,Jan. 1, 2013, 2013 Internation Conference on Computer Medical Application, p. 1-5 (Year: 2013).*

(Continued)

*Primary Examiner* — Hiep V Nguyen
(74) *Attorney, Agent, or Firm* — Finnegan, Henderson, Farabow, Garrett & Dunner LLP

(57) ABSTRACT

Systems and methods are disclosed for visualizing medical data. In one implementation, the systems each comprise a database, a memory that stores a set of instructions and at least one processor in communication with the memory configured to execute the set of instructions so the system may receive the medical data in one or more formats from a plurality of sources, the medical data comprising a plurality of events associated with one or more patients, convert the medical data from the one or more formats to a standardized data format, store the standardized data in the database, receive a query comprising at least one patient characteristic, query the database to identify a patient associated with the at least one patient characteristic, generate a graphical user interface to include the standardized data represented as a timeline of events associated with the identified patient and display the generated graphical user interface.

20 Claims, 19 Drawing Sheets

(51) Int. Cl.
*G06F 16/248* (2019.01)
*G06F 16/9535* (2019.01)

(58) Field of Classification Search
CPC ........ G16H 50/70; G16H 10/60; G16H 40/20;
G16H 10/65
USPC ............................................................ 705/2
See application file for complete search history.

(56) References Cited

U.S. PATENT DOCUMENTS

| | | | |
|---|---|---|---|
| 2008/0221923 A1* | 9/2008 | Shogan | G06Q 50/22 |
| | | | 705/2 |
| 2013/0191165 A1* | 7/2013 | MacDonald | G06F 19/322 |
| | | | 705/3 |
| 2017/0039341 A1 | 2/2017 | Shklarski et al. | |

OTHER PUBLICATIONS

Highcharts:"Make your data come alive"; retrieved from https://www.highcharts.com/; downloaded on Sep. 26, 2017. (6 pages).

Highcharts®: "Everybody's Favorite Charting Library"; retrieved from https://www.highcharts.com/products/highcharts/; downloaded on Sep. 26, 2017. (4 pages).

Highcharts Cloud; retrieved from https://cloud.highcharts.com/; downloaded on Sep. 26, 2017. (12 pages).

Highcharts® Editor: "WYSIWYG Editor for Your APP or CMS"; retrieved from https://www.highcharts.com/products/highcharts-editor/; downloaded on Sep. 26, 2017. (2 pages).

* cited by examiner

COMPANY | Life Sciences Portal | | Company ◊ | | User Name | Sign Out

Dashboards | Data | Patient Journey

Search Patient ID [nscic edm ◊] [Search Patient ID] Search
Advanced Search ▲

Biomarker Status: [All ◊]
Stage: [All ◊]
Drug/Line Combination: [Enter Drug Name] [Enter Line Number]
Age Range at Advanced Diagnosis: [34] [85]
Date of Advanced Diagnosis: [Date Redacted] [Date Redacted]
Patient IDs (100):

710 —
✓
F058DE8201E72
F060869O4F378
F053BC98331C7
F031586CE21D5
F03E6A3DD6171
F0387C4A1BB34
F041F9OD80662
F02240BEB6637
F050DAFC7670F

Welcome to Patient Jou[rney]

This tool enables you to displa[y] data for patients of interest. Each patient journey includes clinical, demographic, and outcomes data for the patient o[r] use the advanced search to find patients that meet certain inclusion criteria.

To get started, please type in a

SYSTEMS AND METHODS FOR VISUALIZING DATA

CROSS REFERENCE TO RELATED APPLICATION

This application claims the benefit of priority of U.S. Provisional Application No. 62/401,138, filed on Sep. 28, 2016. The entire contents of the foregoing application are incorporated herein by reference in its entirely.

BACKGROUND

The diagnosis and treatment of illness involves the intake, processing, and analysis of medical data associated with numerous events. The treatment of long-term illnesses (e.g., cancer) may involve the analysis of a particularly large amount of medical data, which may be gathered from a variety of sources each using a variety of formats and standards, and analyzed by many different health professionals (e.g., physicians, lab technicians, pharmacists, etc.) over the lifetime of a patient. For example, the diagnosis and treatment of cancer in one person may involve the intake, processing, and analysis of medical data pertaining to vital statistics taken by various physicians, laboratory tests performed by different laboratories, and medications prescribed by different physicians and dispensed by different pharmacies over a wide span of time. Proper treatment of an illness requires a thorough understanding of a patient's entire medical history, yet, a physician may have difficulty efficiently analyzing all of the relevant data, particularly for patients with long-term illnesses. This difficulty may arise from data for each patient being maintained in different formats spread across numerous documents and possibly stored in different systems and/or locations, which may not be centrally accessible. Such an arrangement does not give a physician enough time to analyze pertinent data relevant to the patient as it is not in a standardized format and a centralized location.

In recent years, healthcare professionals have begun storing and transmitting patient medical data electronically. The electronic storage of the data has enabled healthcare professionals to record the patient's medical data in a more organized fashion, such that professionals may easily access the data from throughout a patient's medical history. Moreover, healthcare professionals may more easily share patient medical data with one another to collaborate on a course of treatment.

Current systems for processing medical data suffer from drawbacks or disadvantages that inhibit the ability of healthcare professionals to provide optimal care. For example, patient medical data is stored by different healthcare professionals in many different, non-standardized formats, such that convenient comparison and analysis of the data from different sources is difficult. Further, the analysis of the patient's medical data from various sources may require numerous complex queries as the data is usually spread across numerous documents and/or storage locations. Most physicians do not have the necessary freedom of time required to properly analyze and evaluate a patient's entire medical history, and even a cursory effort requires a copious amount of time to organize the patient's entire medical history data into a format that is comprehensible. Still further, since the medical data of a patient includes lab results, outcomes, and medication history, the information is not represented in a single graphical interface for a physician to see the effects of the medication concurrently with the lab results and outcomes, making it difficult for the physician to see a full longitudinal experience of the patient in order to maintain or change dosage of the medication or course of treatment for the patient.

SUMMARY

Consistent with the present disclosure, systems and methods are provided for visualizing electronic data. Embodiments consistent with the present disclosure include computer-implemented systems and methods for receiving patient medical data from a plurality of sources, each utilizing a myriad different format and standard, and generating a standardized timeline to visually represent a patient's medical history, such that the efficacy of the patient's course of treatment may be analyzed, evaluated and a same or modified course of treatment may be proposed. Embodiments consistent with the present disclosure may overcome the drawbacks or problems set forth above.

In accordance with one exemplary embodiment, a system is provided for visualizing medical data. The system includes a database, a memory that stores a set of instructions and at least one processor in communication with the memory and configured to execute the set of instructions to facilitate the system to receive the medical data in one or more formats from a plurality of sources over a network, the medical data comprising a plurality of events associated with one or more patients, convert the medical data from the one or more formats to a standardized data format, store the standardized data in the databases, receive a query comprising at least one patient characteristic, query the databases to identify a patient associated with the at least one patient characteristic, generate a graphical user interface to include the standardized data as a timeline of events associated with the identified patient and display the generated graphical user interface.

In accordance with another exemplary embodiment, a computer-implemented method for visualizing medical data is provided. The method is performed by one or more processors. The method comprising, receiving the medical data in one or more formats from a plurality of sources over a network, the medical data comprising a plurality of events associated with one or more patients, converting the medical data from the one or more formats to a standardized data format, storing the standardized data in a database, receiving a query comprising at least one patient characteristic, querying the databases to identify a patient associated with the at least one patient characteristic, generating a graphical user interface to include the standardized data as a timeline of events associated with the identified patient and displaying the generated graphical user interface.

In accordance with a further exemplary embodiment, a computer-readable storage medium comprising a set of instructions executable by at least one processor to perform a method for visualizing medical data is provided. The method comprising, receiving the medical data in one or more formats from a plurality of sources over a network, the medical data comprising a plurality of events associated with one or more patients, converting the medical data from the one or more formats to a standardized data format, storing the standardized data in a database, receiving a query comprising at least one patient characteristic selected from a group comprising a patient identifier, a biomarker, a status, a drug and line of therapy combination, an age of patient at diagnosis, and a date of diagnosis, querying the database to identify a patient associated with the at least one patient characteristic, generating a graphical user interface including a timeline of events associated with the identified entity and displaying the generated graphical user interface.

In accordance with yet another exemplary embodiment, a system for visualizing medical data is disclosed. The system comprising a database, one or more data sources, one or more client devices and an apparatus communicatively connected to the database, data sources and client devices over a network. The apparatus comprising a memory to store a set of instructions and one or more processors in communication with the memory and configured to execute the set of instructions such that the apparatus can receive, from the one or more data sources, the medical data in one or more formats, the medical data comprising a plurality of events associated with one or more patients, convert the medical data from the one or more formats to a standardized data format, store the standardized data in the database, receive a query comprising at least one patient characteristic selected from a group comprising patient ID, biomarker, status, drug and line of therapy combination, age of the patient at diagnosis and date of the diagnosis, query the one or more databases to identify a patient associated with the at least one patient characteristic, generate a graphical user interface to include the standardized data as a timeline of events associated with the identified patient and display the generated graphical user interface.

Consistent with other disclosed embodiments, non-transitory computer readable storage media may store program instructions, which are executed by at least one processing device and perform any of the methods described herein.

Before explaining certain embodiments of the present disclosure in detail, it is to be understood that the disclosure is not limited to the arrangements of the components set forth in the following description or illustrated in the drawings. The disclosure is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the conception and features upon which this disclosure is based may readily be used as a basis for designing other structures, methods, and systems for carrying out the several purposes of the present disclosure. Furthermore, the claims should be regarded as including such equivalent constructions insofar as they do not depart from the spirit and scope of the present disclosure.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 6 is another exemplary graphical user interface, consistent with embodiments of the present disclosure.

FIG. 7 is another exemplary graphical user interface, consistent with the embodiments of the present disclosure.

FIG. 10 is another exemplary graphical user interface, consistent with the embodiments of the present disclosure.

Figure 12:
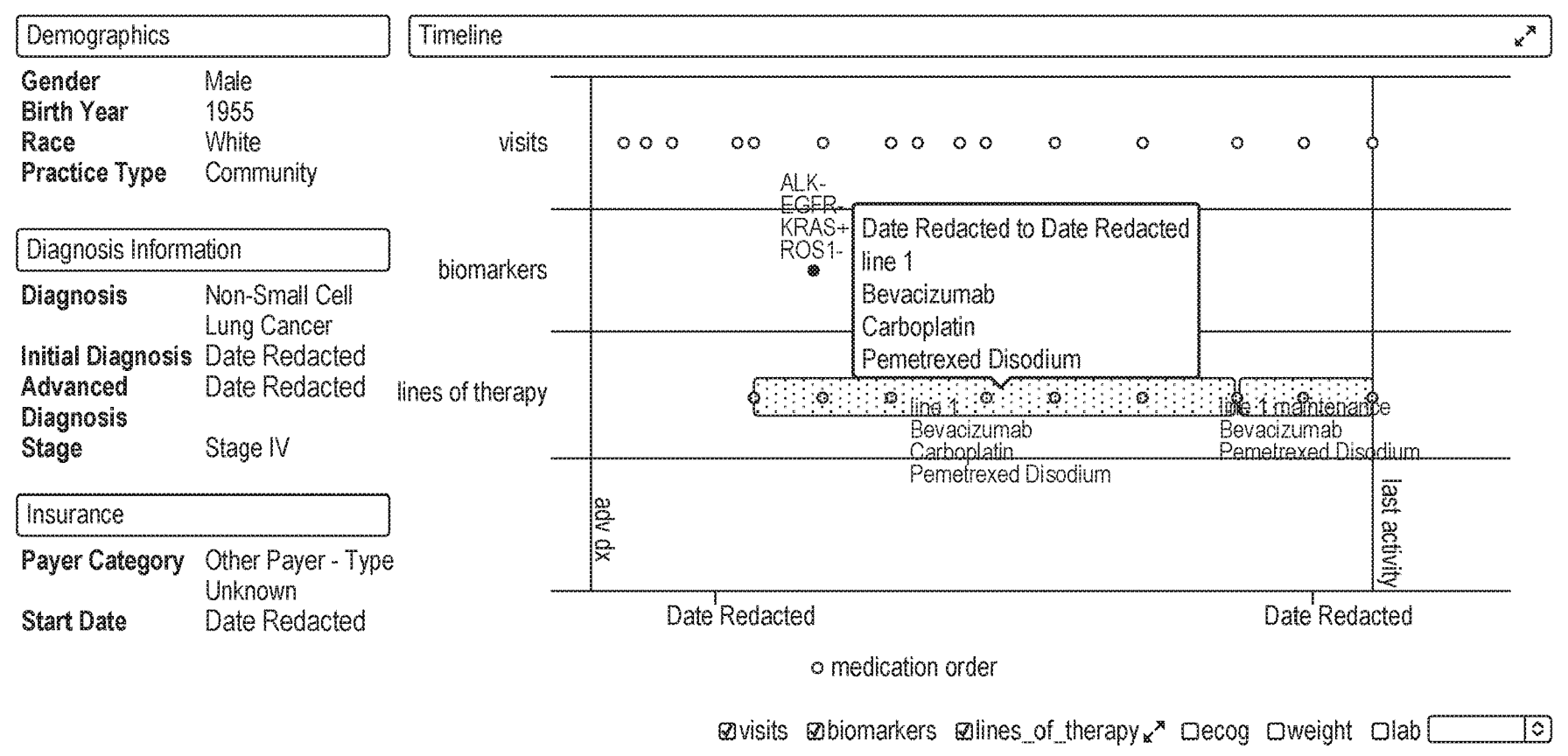

FIG. 12 is another exemplary graphical user interface, consistent with the embodiments of the present disclosure.

DETAILED DESCRIPTION

Figure 1:
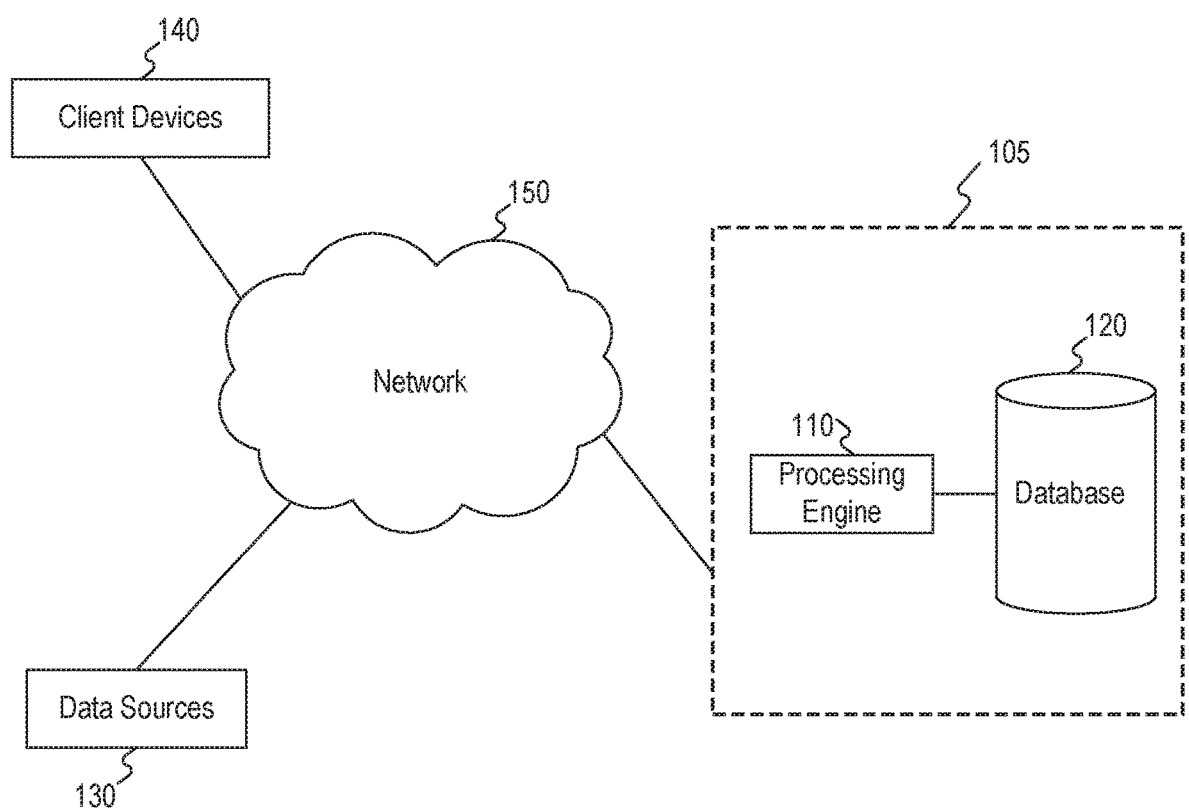
FIG. 1 is a block diagram illustrating an exemplary system environment for implementing embodiments consistent with the present disclosure.

Reference will now be made in detail to the exemplary embodiments implemented according to the disclosure, the examples of which are illustrated in the accompanying drawings. Wherever possible, the same reference numbers will be used throughout the drawings to refer to the same or like parts.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Embodiments of the present disclosure provide systems and methods for visualizing electronic data. The disclosed embodiments enable a user to visualize key components of a patient's health over time, including disease characteristics, treatment, outcomes, and demographics. The disclosed embodiments facilitate the exploration of patient medical data and allow a user to quickly understand the chronology of and identify discrepancies in the data that would not be readily apparent through prior systems (e.g., review of patient charts). The disclosed embodiments also enable the user to search for a patient cohort (or group) of interest and visualize patient data for all patients that meet the criteria associated with the cohort. A user of the disclosed systems and methods may encompass any individual who may wish to access a patient's clinical experience and/or quickly get up to speed on a patient's clinical experience. Thus, throughout this disclosure, references to a "user" of the disclosed systems and methods may encompass any individual, such as a physician, a quality assurance department at a health care institution, and/or the patient.

Embodiments of the present disclosure provide numerous advantages over prior systems. For example, the disclosed embodiments enable a user to quickly visualize and summarize data for a patient of interest in a standardized format. The disclosed embodiments enable a user to screen a large amount of patient data to identify individual patients meeting specified criteria. Users may use the output data to identify edge cases of patients in a cohort and further analyze those patients. The disclosed embodiments organize data from a variety of sources (e.g., structured/unstructured data sources, third-party linked data), each using a myriad of formats and standards, and present that data in a standardized manner on a graphical user interface. Additional information regarding processing unstructured documents and extracting data from unstructured documents is included in U.S. patent application Ser. No. 15/211,250, filed Jul. 15, 2016 (published as US 2017/0039341), which is incorporated herein by reference in its entirety.

The disclosed embodiments allow users to compare events that occur over time to see how the events relate to one another. For example, a user may compare a laboratory test result against a medication administration and further compare each of those events to data collected during an office visit. The disclosed embodiments may also be used to hasten patient identification, eligibility determinations, and enrollment for clinical trials. Thus, the disclosed systems and methods may provide a means of investigating questions by viewing data points in context and digging deeper to see additional details about a specific patient or refine the cohort of patients, and the disclosed systems and methods may further allow a user to take data from detailed tables and interpret it at a patient-level in a way that is much more informative.

FIG. 1 illustrates an exemplary system environment 100 for implementing embodiments of the present disclosure. As shown in FIG. 1, system environment 100 includes a number of components. It will be appreciated from this disclosure that the number and arrangement of these components is exemplary and provided for purposes of illustration. Other arrangements and numbers of components may be utilized without departing from the teachings and embodiments of the present disclosure.

As shown in FIG. 1, the exemplary system environment 100 includes a system 105. System 105 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 105 may include a processing engine 110 and one or more databases 120, which are illustrated in a region bounded by a dashed line for system 105 in FIG. 1.

In one embodiment, system 105 may transmit and/or receive patient medical data to/from various other components, such as one or more data sources 130 and client devices 140. More specifically, system 105 may be configured to receive and store the data transmitted over a network 150 (e.g., Internet, Intranet, WAN, LAN, cellular, etc.) from various data sources, including data sources 130, process the received data, and transmit search results based on the processing to client devices 140.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

As described above, system 105 may be configured to receive patient medical data over a network 150, process and analyze the data, and provide results of the analysis to client devices 140 over the network 150. For example, system 105 may receive patient medical data from data sources 130 or elsewhere on network 150. The data provided to system 105 from data sources 130 (or elsewhere) may include structured data, such as gender, birth year, race, visit date, practice type, insurance carrier and start date, office visits, medication orders, medication administrations, Eastern Cooperative Oncology Group (ECOG) performance status (i.e., ECOG score), weight, lab results, etc.; unstructured data, such as diagnosis date, first activity date, stage at diagnosis, advanced diagnosis date, metastatic diagnosis date (usually for cancer patients), biomarker results, tumor progression and response (usually for cancer patients), oral medications, and laboratory details regarding the lab tests, etc.; and derived data, such as date of death, lines of therapy, and last activity date, outcomes, etc. In one embodiment, the unstructured data is captured by an abstraction process, while the structured data is entered by the health care professional or calculated using algorithms. In one embodiment, data sources 130 may include medical care providers (e.g., physicians, hospitals), laboratories, insurance companies, and any other source of patient data.

System 105 may also communicate with client devices 140 over network 150. For example, client devices 130 may transmit queries for patient medical data over network 150 to system 105. In one embodiment, a query for the data may include patient characteristics, such as patient identifier (ID), biomarker status, stage, drug/line combination, lines of therapy, age range at advanced diagnosis, date of advanced diagnosis, where did the test sample come from, details on the actual Epidermal Growth Factor Receptor (EGFR) mutation, where was the test tissue collected from (for cancer tests), type of assay, like straining intensity, if metastasized and if spread (for cancer patients), etc. System 105 may query database 120 to identify a patient matching the query parameters and transmit the medical data associated with the matching patient over network 150 to client devices 140.

In accordance with certain embodiments, system 105 may include one or more processing engines 110, which may be configured to transmit medical data over network 150 to and from data sources 130 and client devices 140. In one embodiment, each processing engine 110 may store data received from data sources 130 and client devices 140 in one or more databases 120. Databases 120 may be any suitable combination of large scale data storage devices, which may optionally include any type or combination of slave databases, load balancers, dummy servers, firewalls, back-up databases, and/or any other desired database components. Each processing engine 110 may also access data stored by databases 120 in order to process queries received from client devices 140. For example, processing engine 110 may access from databases 120 entity data (e.g., patient medical data) received from data sources 130 and generate a user interface that visualizes the entity data (e.g., on a timeline) in a standardized format. Processing engine 110 may transmit the generated user interface to client device 140 for display to a user.

It will be appreciated that any suitable configuration of software, processors, data storage devices, and networks may be selected to implement the components of system environment 100 and features of related embodiments.

Figure 2:
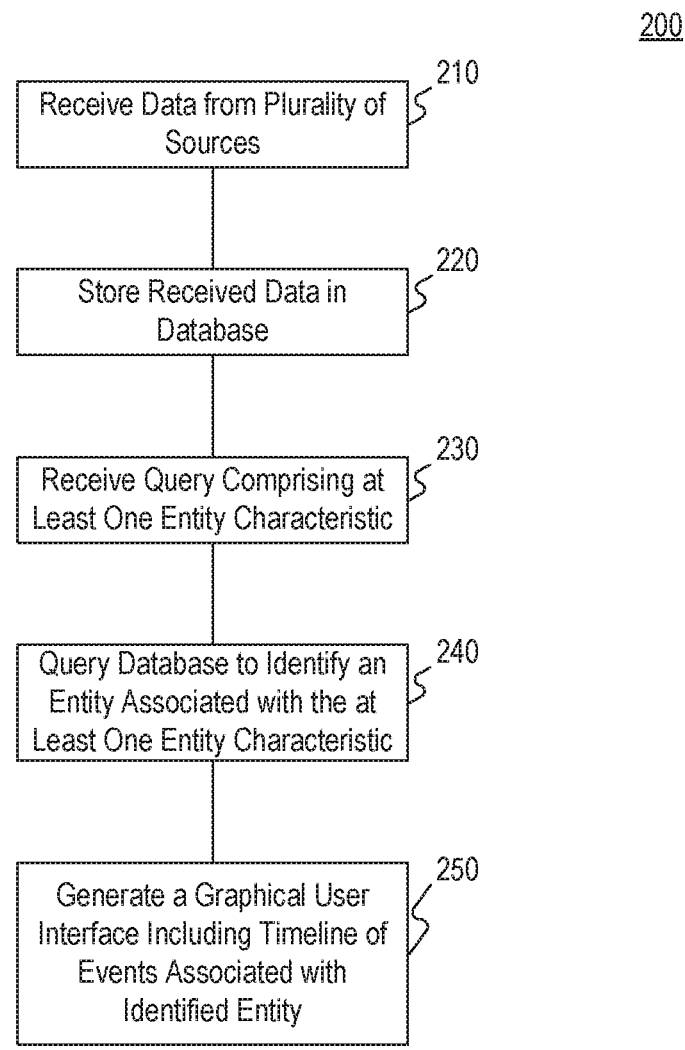
FIG. 2 is a flow diagram representing an exemplary process for visualizing data, consistent with embodiments of the present disclosure.

FIG. 2 illustrates a flow of an exemplary process 200 for visualizing a patient's medical data, consistent with embodiments of the present disclosure. The steps associated with this exemplary process may be performed by the components of FIG. 1. For example, the steps associated with the exemplary process of FIG. 2 may be performed by processing engine 110 and/or databases 120 of system 105 with data from data sources 130 received via network 150 illustrated in FIG. 1.

At step 210, the patient's medical data is received from a plurality of sources (e.g., data sources 130) over a network (e.g., network 150). For example, at step 210, processing engine 110 of system 105 may receive the data. The data may comprise a plurality of events associated with one or more entities. According to some embodiments, the received data comprises a plurality of medical records and the one or more entities comprise one or more patients. In one embodiment, each of the plurality of events is associated with a date and a data point selected from office visits, biomarkers, lines of therapy, ECOG scores, weight, lab results, and outcomes based on line of therapy and medications, etc.

In one embodiment, the received data comprises structured data and unstructured data. Structured data may include data received from an Electronic Health Record (EHR) system. Exemplary structured data points may include office visits, biomarkers, lines of therapy, ECOG scores, weights, and lab results based on lines of therapy and medications, etc. Exemplary unstructured data points may include data from a patient's chart, such as diagnosis date, stage at diagnosis, advanced diagnosis date, metastatic diagnosis date, biomarker results, tumor progression (in case of cancer patients), tumor response (in case of cancer patients), oral medications, etc. In one embodiment, unstructured data may be determined by receiving an electronic scan of patient data and processing the scanned data to identify and format certain aspects of the patient data. The received data may also include derived data, which may comprise data derived from one or more other data points (e.g., data derived from analysis of structured or unstructured data). Exemplary points of derived data may include date of death, lines of therapy, last activity date, etc.

At step 220, the received data is stored in a database (e.g., processing engine 110 may store the received data in database 120). In one embodiment, standardized data is stored in the database. Moreover, in one embodiment, the original (i.e., raw) data and standardized data may both be stored in the database.

At step 230, a query comprising at least one entity characteristic is received. For example, a user of a device (e.g., client device 140) may enter at least one characteristic of an entity into a form (e.g., a web-based form) and submit the form to a server (e.g., processing engine 110) for processing. In one embodiment, the at least one entity characteristic is a patient characteristic selected from the group consisting of patient ID, biomarker status, drug and line combination, age at diagnosis, date of diagnosis, etc.

At step 240, the database is queried to identify an entity associated with the at least one entity characteristic. For example, a server (e.g., processing engine 110) may convert a query received from a client device (e.g., client device 140) into a language (e.g., structured query language or SQL) appropriate for a connected database (e.g., database 120) and submit the query to the database. In one embodiment, a query may return multiple results. For example, multiple entities may possess the at least one entity characteristic received from a client device. According to one embodiment, the data may be retrofitted to include data appropriate for the query. Accordingly, a list of matching entities may be provided to the client device. The user of the client device may select one of the entities from the list of matching entities to obtain additional information regarding the selected entity. According to one embodiment, the user may be provided one or more filters. For example, data filtering may allow the user to refine the received data even further to include only the data needed for a specific task and to exclude data that can be repetitive or irrelevant.

At step 250, a user interface including a timeline associated with the identified entity is generated by, for example, processing engine 110. In one embodiment, the timeline comprises a plurality of rows and each row comprises events associated with the same data point. For example, if four data points are stored in the database for a patient identified by the query, then the timeline may display four rows (e.g., one for each data point). Each row may further comprise events associated with that data point. For example, if weight data was obtained eight times during a patient's course of treatment, the timeline may present a row indicating eight weight measurements for the patient associated with times that the measurements were taken. Similarly, if lab results were obtained for a patient four times during a course of treatment, four values corresponding to the measured characteristic (e.g., hemoglobin, neutrophils, creatinine, albumin, or bilirubin) may be displayed in the same row within a timeline. Moreover, the weights and lab results may be displayed on the timeline together to facilitate improved analysis of the data.

In one embodiment, a user may select an event depicted on the timeline. In response to receiving the selection of the event, a window may be generated within the user interface that comprises additional details associated with the event. For example, if a user selects an event associated with analysis of a biomarker performed on a given date, a window may be generated containing additional details associated with that analysis (e.g., status, type of specimen collected, date specimen collected, date result determined, date result reported).

In one embodiment, the received data comprises at least one line of therapy for a patient and at least one indicator of a patient response to the at least one line of therapy. Based on this data, a modified line of therapy may be determined. In one embodiment, the generated user interface may be modified to add the modified line of therapy to the timeline. In another embodiment, a modification to a line of therapy may be received from a user and stored in the database. The generated user interface may be modified to add the modified line of therapy to the timeline. For example, a physician may review the timeline presented for a patient and, based on that review, determine to modify the line of therapy for the patient in view of subpar results noted in response to a previous line of therapy. The physician may input the modified line of therapy into a client device and send the modified line of therapy to another device (e.g., a server), such that it may be stored in association with the patient's other health records in a database accessible by the device. The timeline may be modified to reflect this change to the line of therapy.

Figure 3:
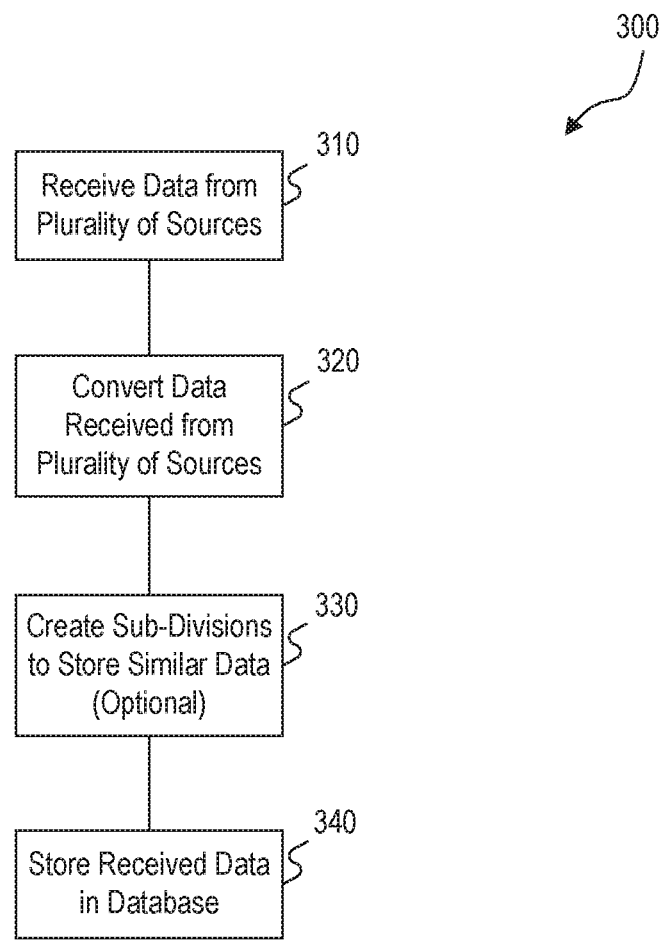
FIG. 3 is a flow diagram representing an exemplary process for storing data in a database, consistent with embodiments of the present disclosure.

FIG. 3 illustrates a flow of an exemplary process 300 for storing a patient's medical data in a database, consistent with embodiments of the present disclosure. The steps associated with this exemplary process may be performed by the components of FIG. 1. For example, the steps associated with the exemplary process of FIG. 3 may be performed by processing engine 110 and/or databases 120 of system 105 using data from data sources 130 received via network 150 illustrated in FIG. 1.

At step 310, the patient's medical data is received from a plurality of sources (e.g., data sources 130) over a network (e.g., network 150). For example, at step 310, processing engine 110 of system 105 may receive the data. As described, the data may comprise a plurality of events associated with one or more entities, and the received data may include structured data and unstructured data.

At step 320, the received data is processed. In one embodiment, the received data may be standardized. In particular, the data received from different sources may be converted to one or more common formats. For example, some data sources may store weight data in kilograms, whereas other data sources may store weight data in pounds. Accordingly, weight data (and other data points) may be converted to a standard format (e.g., kilograms), such that data from different data sources may be more easily compared when presented to the user. In another embodiment, received data format may be standardized. In particular, the data received from different sources may be converted to one or more common formats for storing the data in a database. For example, data gathered from the Internet may be received in an HTML format, whereas the original format of the data could be PDF. Accordingly, data received in a variety of computing formats may be converted to a standardized format for storing the standardized data in a database and for retrieving the data using standardized data query languages.

At step 330, which may be an optional step, the standardized data may be sorted into sub-divisions, wherein each sub-division holds similar data. According to one embodiment, data received from a common group of medical services, e.g., laboratory testing facilities, may be sorted by test type, test abnormalities, test location, etc. For example, a sub-division of test location will include data pertaining to the details of the laboratory. According to another embodiment, the sub-divisions may be further divided. For example, a sub-division of test type may include further sub-divisions of blood tests, urine tests, etc.

At step 340, standardized data, including standardized data in the sub-divisions is stored in a database (e.g., processing engine 110 may store the received data in database 120). As described, the original (i.e., raw) data and standardized data may both be stored in the database as well.

Figure 4:
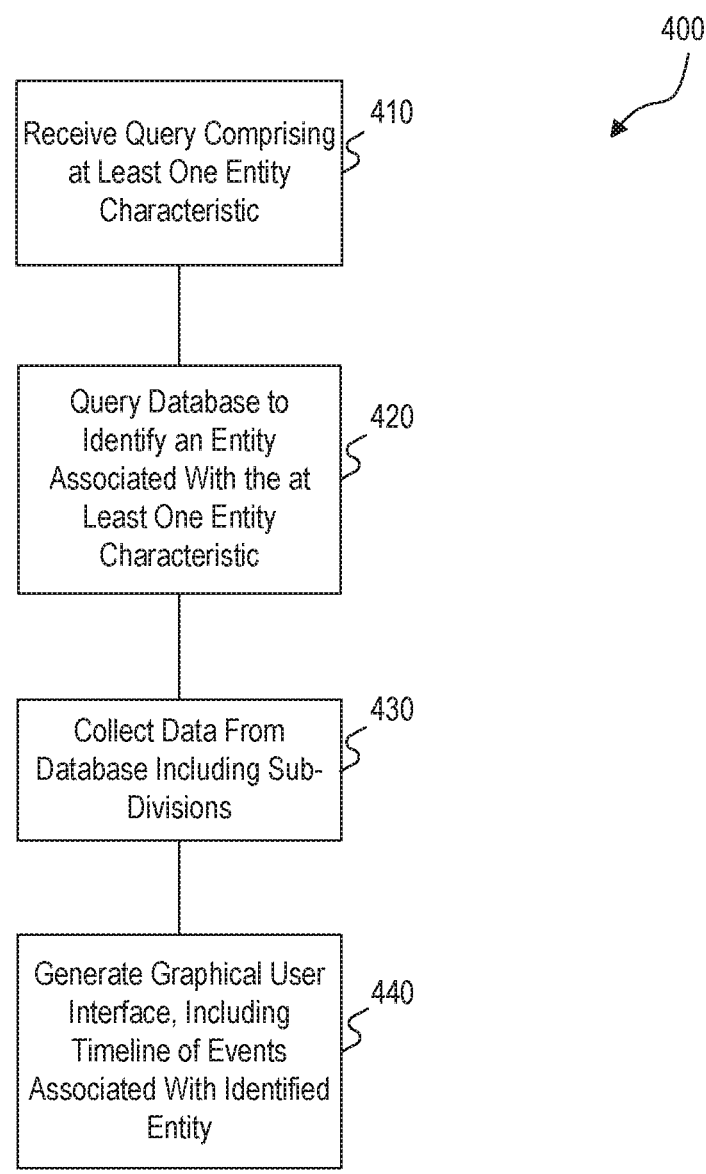
FIG. 4 is a flow diagram representing an exemplary process for displaying data from a database, consistent with embodiments of the present disclosure.

FIG. 4 illustrates a flow of an exemplary process 400 for displaying a patient's medical data from a database, consistent with embodiments of the present disclosure. The steps associated with this exemplary process may be performed by the components of FIG. 1. For example, the steps associated with the exemplary process of FIG. 4 may be performed by processing engine 110 and/or databases 120 of system 105 to display standardized data on client devices 140 received via network 150 illustrated in FIG. 1.

At step 410, a query comprising at least one entity characteristic is received. For example, a user of a device (e.g., client device 140) may enter at least one characteristic of an entity into a form (e.g., a web-based form) and submit the form to a server (e.g., processing engine 110) for processing. In one embodiment, the at least one entity characteristic may include a patient characteristic selected from the group consisting of patient ID, biomarker status, drug and line combination, age at diagnosis, date of diagnosis, etc.

At step 420, the database is queried to identify an entity associated with the at least one entity characteristic. For example, a server (e.g., processing engine 110) may convert a query received from a client device (e.g., client device 140) into a language (e.g., structured query language or SQL) appropriate for a connected database (e.g., database 120) and submit the query to the database.

At step 430, the data, including data within sub-divisions is collected for display. In one embodiment, a query may return multiple results. For example, multiple entities may possess the at least one entity characteristic received from a client device. According to one embodiment, the data may be customized to include data appropriate for the query. Accordingly, a list of matching entities may be provided to the client device. The user of the client device may select one of the entities from the list of matching entities to obtain additional information regarding the selected entity. According to one embodiment, the user may be provided one or more filters. For example, data filtering may allow the user to refine the received data even further to include only the data needed for a specific task and to exclude data that can be repetitive or irrelevant.

At step 440, a user interface including a timeline associated with the identified entity is generated by, for example, processing engine 110. As described, the timeline may include a plurality of rows and each row comprises events associated with the same data point. As also described, a user may select an event depicted on the timeline. In response to receiving the selection of the event, a window may be generated within the user interface that comprises additional details associated with the event.

As also described, the received data may include at least one line of therapy for a patient and at least one indicator of a patient response to the at least one line of therapy. Based on this data, a modified line of therapy may be determined. The generated user interface may be modified to add the modified line of therapy to the timeline. For example, a physician may review the timeline presented for a patient and, based on that review, determine to modify the line of therapy for the patient in view of subpar results noted in response to a previous line of therapy. The physician may input the modified line of therapy into a client device and send the modified line of therapy to a server, such that it may be stored in association with the patient's other health records in the database. The timeline may be modified to reflect this change to the line of therapy.

Figure 5:
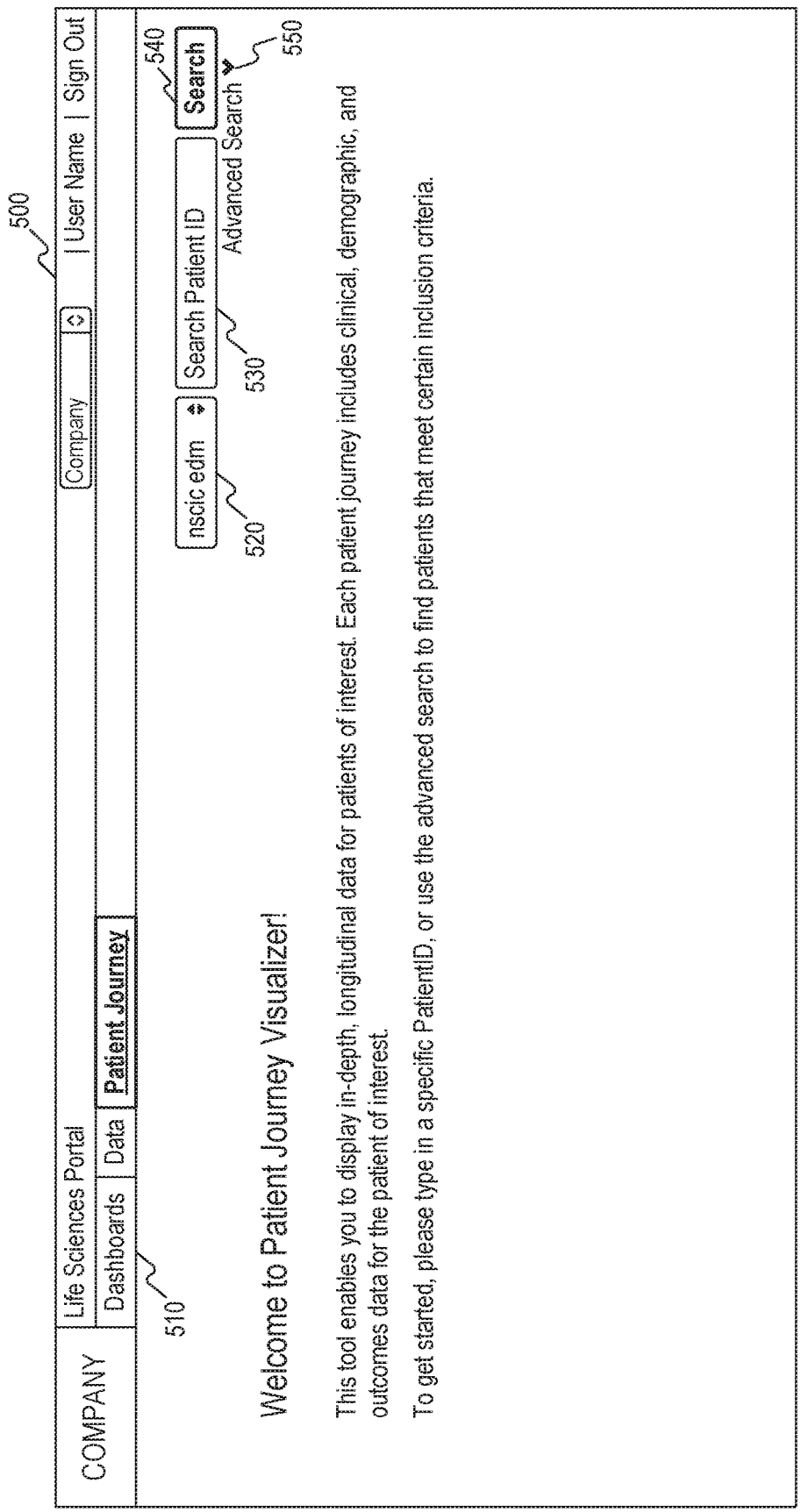
FIG. 5 is an exemplary graphical user interface, consistent with embodiments of the present disclosure.

FIG. 5 illustrates an exemplary graphical user interface 500, consistent with embodiments of the present disclosure. Graphical user interface 500 illustrates an example of an interface or portal generated by a computing system (e.g., processing engine 110) that can be displayed on a device (e.g., client devices 140) for viewing by a user. Interface 500 can enable the user to query the system (e.g., system 105) for patient medical data. In the exemplary embodiment of FIG. 5, interface 500 includes tabs 510, data source selector 520, patient identifier input 530, search button 540, and advanced search option 550. It will be readily understood from this disclosure that the number and arrangement of these elements is exemplary and that modifications can be made without departing from the teachings and embodiments consistent with the present disclosure.

Tabs 510 may enable a user to select a particular application, portal, or interface of interest to the user. The exemplary tabs shown in FIG. 5 are for Dashboards, Data, and Patient Journey. In FIG. 5, the Patient Journey tab has been highlighted, i.e., bold-underlined to indicate that the user has selected the Patient Journey tab. Accordingly, the information displayed in user interface 500 corresponds to data from the Patient Journey tab.

Data source selector 520 enables the user to select a data source to search from a list of available data sources. In one embodiment, data source selector 520 may display a list of local and remote databases that store patient medical data. Patient identifier input 530 enables a user to specify a patient identifier (ID). The patient ID may include a medical record number or any other identifier used to associate a patient with his or her personal health data. The user may select search button 540 to query the data source selected using data source selector 520 for the patient ID entered into patient identifier input 530. Alternately, the user may select advanced search option 550 to present additional input fields that may be used to query one or more sources for patient data (as illustrated in FIG. 6).

Figure 6:
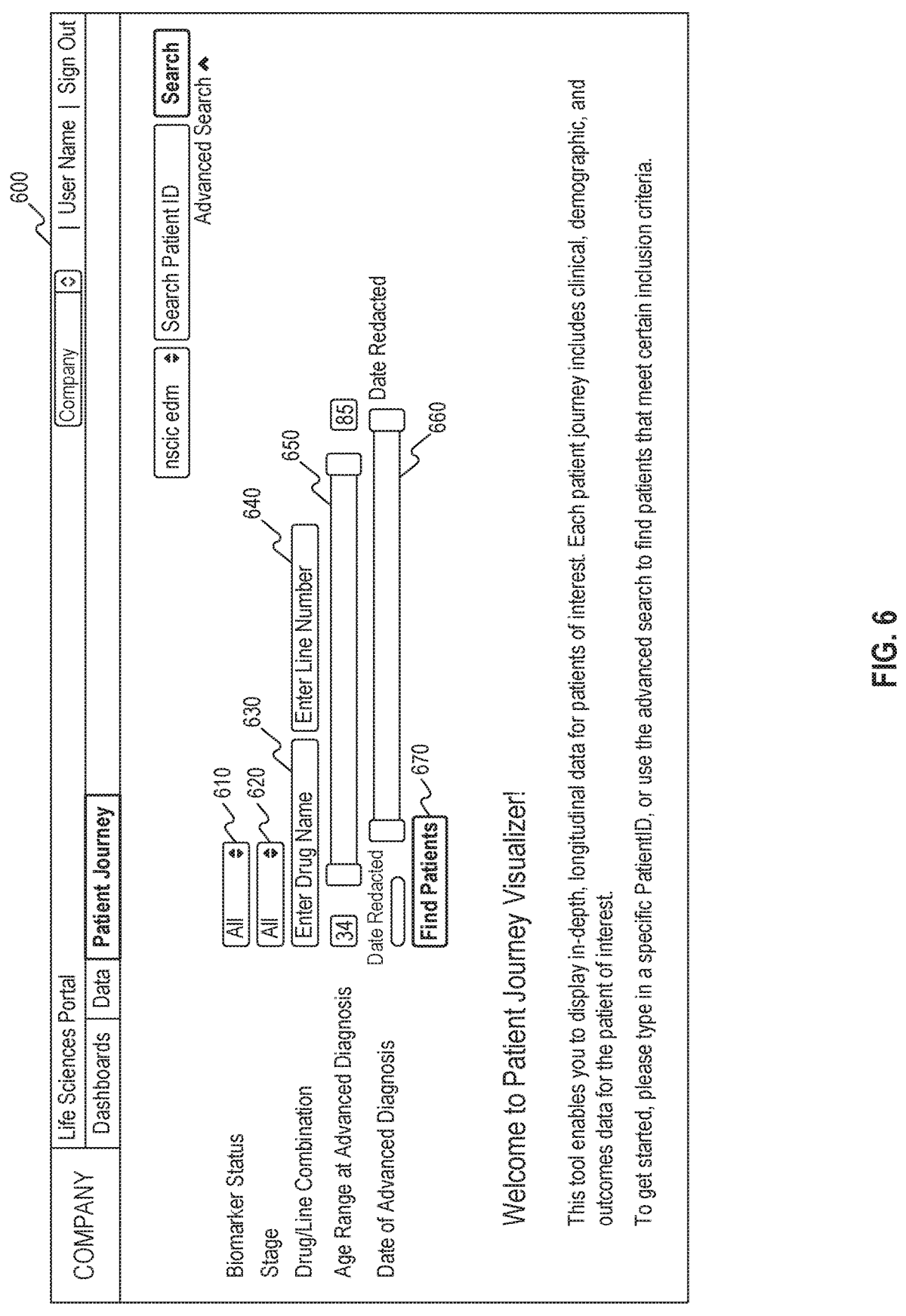

FIG. 6 illustrates another exemplary graphical user interface 600, consistent with embodiments of the present disclosure. User interface 600 illustrates an example of an interface or portal generated by a computing system (e.g., processing engine 110) that can be displayed on a device (e.g., client devices 140) for viewing by a user. Interface 600 can enable the user to transmit an advanced query for patient data to the data system (e.g., system 105). In the exemplary embodiment of FIG. 6, interface 600 includes biomarker status selector 610, stage selector 620, drug input 630, line input 640, age range selector 650, date range selector 660, and find patient button 670. Interface 600 may also include one or more elements depicted in interface 500, such as tabs 510, data source selector 520, patient identifier input 530, search button 540, and advanced search option 550. It will be readily understood from this disclosure that the number and arrangement of these elements is exemplary and that modifications can be made without departing from the teachings and embodiments consistent with the present disclosure.

Biomarker status selector 610 enables the user to select a biomarker status. Stage selector 620 enables the user to select a stage of illness. Drug input 630 and line input 640 enable the user to identify a drug name and line number, respectively. Age range selector 650 and date range selector 660 enable the user to specify a range of ages and dates at or during which a patient was given an advanced diagnosis of an illness. The user may select find patient button 670 to query the system for patient data that meets the parameters specified in elements 610-660. For example, in response to user selection of find patient button 670, the system may query the data sources selected in data source selector 520 using query values specified in elements 610-660.

FIG. 7 illustrates another exemplary graphical user interface 700, consistent with embodiments of the present disclosure. User interface 700 illustrates an example of an interface or portal generated by a computing system (e.g., processing engine 110) that can be displayed on a device (e.g., client devices 140) for viewing by a user. Interface 700 can enable the user to select a patient for analysis. In the exemplary embodiment of FIG. 7, interface 700 includes a patient listing 710. Patient listing 710 may include patient IDs returned in response to a search performed in response to a user's selection of search button 540 or find patient button 670. In response to user selection of a patient ID from patient listing 710, the user device may submit a query to a patient data system (e.g., system 105) for patient health data associated with the selected patient ID. It will be readily understood from this disclosure that the number and arrangement of these elements is exemplary and that modifications can be made without departing from the teachings and embodiments consistent with the present disclosure.

Figure 8:
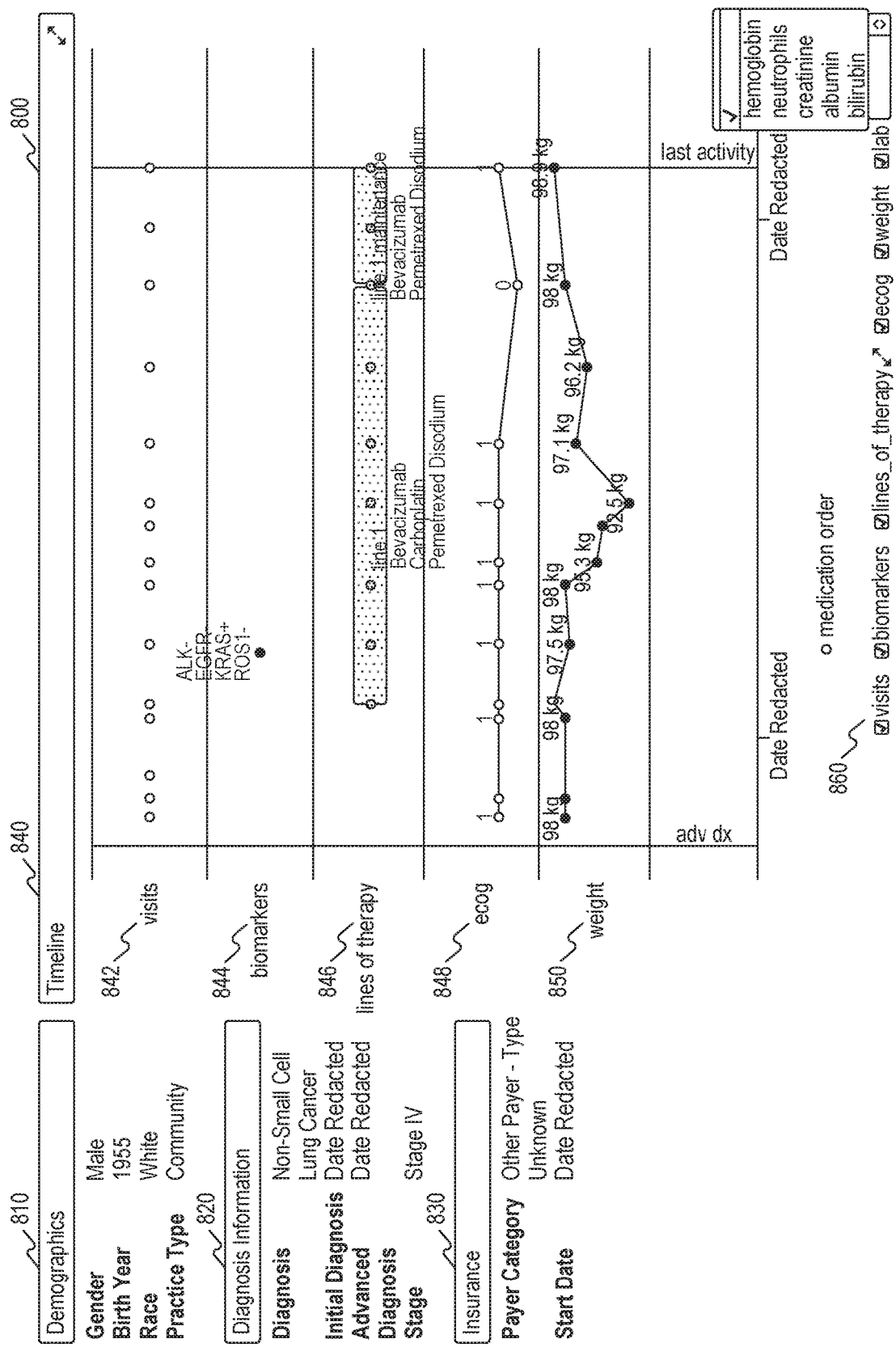
FIG. 8 is another exemplary graphical user interface, consistent with the embodiments of the present disclosure.

FIG. 8 illustrates another exemplary graphical user interface 800, consistent with embodiments of the present disclosure. User interface 800 illustrates an example of an interface or portal generated by a computing system (e.g., processing engine 110) that can be displayed on a device (e.g., client devices 140) for viewing by a user, e.g., a physician. Interface 800 can enable the user to visualize health data associated with a selected patient. In the exemplary embodiment of FIG. 8, interface 800 includes demographic information 810, diagnosis information 820, insurance information 830, timeline 840 (including data for visits 842, biomarkers 844, lines of therapy 846, Eastern Cooperative Oncology Group (ECOG) score 848, and weight 850), and data selectors 860. It will be readily understood from this disclosure that the number and arrangement of these elements is exemplary and that modifications can be made without departing from the teachings and embodiments consistent with the present disclosure.

In the exemplary user interface shown in FIG. 8, static information (i.e., information that does not usually change over time) is displayed in a tabular format along the left side of the interface. Exemplary static information may include demographic information 810, diagnosis information 820, and insurance information 830. Demographic information 810 may include various demographic information for a selected patient, including, for example, gender, birth year, race, and practice type. Diagnosis information 820 may include various diagnosis information associated with a selected patient. For example, diagnosis information 820 may include an identification of a diagnosed illness of the patient, a date of initial diagnosis, a date of advanced diagnosis, a stage of illness, etc. Insurance information 830 may include insurance information associated with a selected patient, including payer category and start date.

Dynamic information (i.e., information that may vary over time) may be displayed in timeline 840. Timeline 840 may display various events associated with data points in a patient's medical history. In the exemplary timeline depicted in FIG. 8, the data displayed in timeline 840 corresponds to data collected between the date of advanced diagnosis with an illness through the date of last activity associated with the patient. In one embodiment, certain point-in-time data elements, such as advanced diagnosis date, date of death, and last activity date, may be rendered as vertical lines that cover the full Y-axis of the timeline. The exemplary interface depicted in FIG. 8 includes information corresponding to five data points: visits 842, biomarkers 844, lines of therapy 846, ECOG score 848, and weight 850.

Visits 842 may render each office visit from structured data as a small circle centered on the X-axis at the date of the visit. Biomarkers 844 may render results from unstructured biomarker test reports as circles centered on the X-axis at the date the results were reported with specific biomarker results that were found displayed surrounding the circle. Lines of therapy 846 may incorporate structured medication order and administration data and derived lines of therapy into a single unified visualization, with each line of therapy rendered as a shaded bar covering the time period of that line and the order and administration data rendered as circles inside of the shaded bar for the line they belong to. In one embodiment, lines of therapy 846 may also be expanded to show the orders and administrations for different medicines separately. An outcomes section (not shown) may show unstructured information about tumor progression and response (for cancer patients) with shaded bars covering the time periods assessed for progression or response, overlaid with small icons centered on the X-axis at the date an oncologist assessed the progression or response. Different levels of progression or response may be shown by vertically offsetting the icons. ECOG score 848, weight 850, and lab results (not shown) may depict the relevant structured data as a line graph. Other structured, unstructured and derived data elements, including data from third-party sources, may be added across the timeline. For example, in case of cancer types, data points per cancer type based on clinical input from oncologists are curated to highlight the most relevant data points. Since different labs are relevant for different types of cancer, e.g., CA 19-9 is referenced during treatment of pancreatic cancer, while CA 15-3 is more relevant for breast cancer, these references can be shown as additional data points on the timeline.

Further, each disease may highlight particular patient properties that may be especially relevant. These highlighted properties may be displayed on the timeline.

For example, a function for breast cancer as follows may be executed:

add_data_to_static_display('diagnosis_information',
      [{'name': 'Menopausal Status', 'field': 'menopausal-status'}])

and may highlight a menopausal status of a patient that may be relevant for the patient. Or for lung cancer, the following function may be executed:

add_data_to_static_display('diagnosis_information',
      [{'name': 'Smoking Status', 'field': 'smokingstatus'}])

may highlight a smoking status of a patient that may be relevant for the patient.

As another example, mouse-overs may be used to provide additional information about a particular data point, such as results of a biomarker test. As yet another example, each category of data displayed may be toggled on and off by a user to hone in on areas of interest.

Further, other data points may be curated per patient in order to highlight the ones that are most important to the overall patient journey. For example, a patient may have received 50 different medications, many of which can be pain medications or medications used to treat side effects of cancer or cancer treatment. It would be difficult in conventional systems to visualize all of these medications at once. According to one embodiment, a visualization tool, e.g., timeline 840, may limit the medication visual list to only the most relevant. According to another embodiment, additional medications can also be added to the timeline for specific projects.

Data selectors 860 enable the user to select which data points are represented in timeline 840. In the exemplary interface depicted in FIG. 8, the data selectors corresponding to visits, biomarkers, lines of therapy, ECOG score, and weight are selected; thus, each of these data points may be displayed in timeline 640. Data selectors 660 also enable the user to select lab results for visualizing in timeline 640. In the exemplary interface depicted in FIG. 8, the user may select to view hemoglobin, neutrophils, creatinine, albumin, or bilirubin levels for the selected patient. Once selected, these levels may be depicted as another row in the timeline (e.g., below the row for weight).

Figure 9:
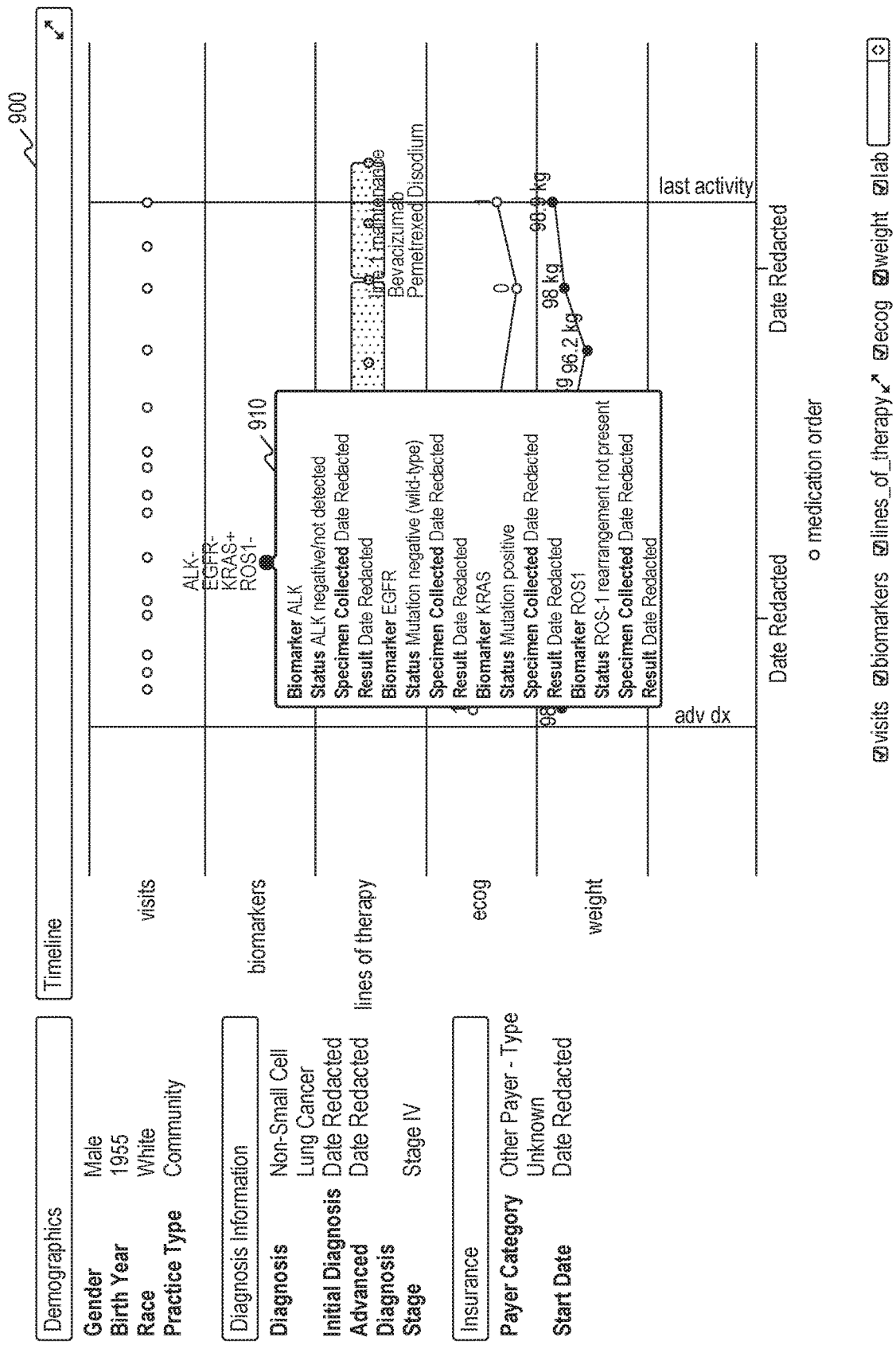
FIG. 9 is another exemplary graphical user interface, consistent with the embodiments of the present disclosure.
Figure 11:
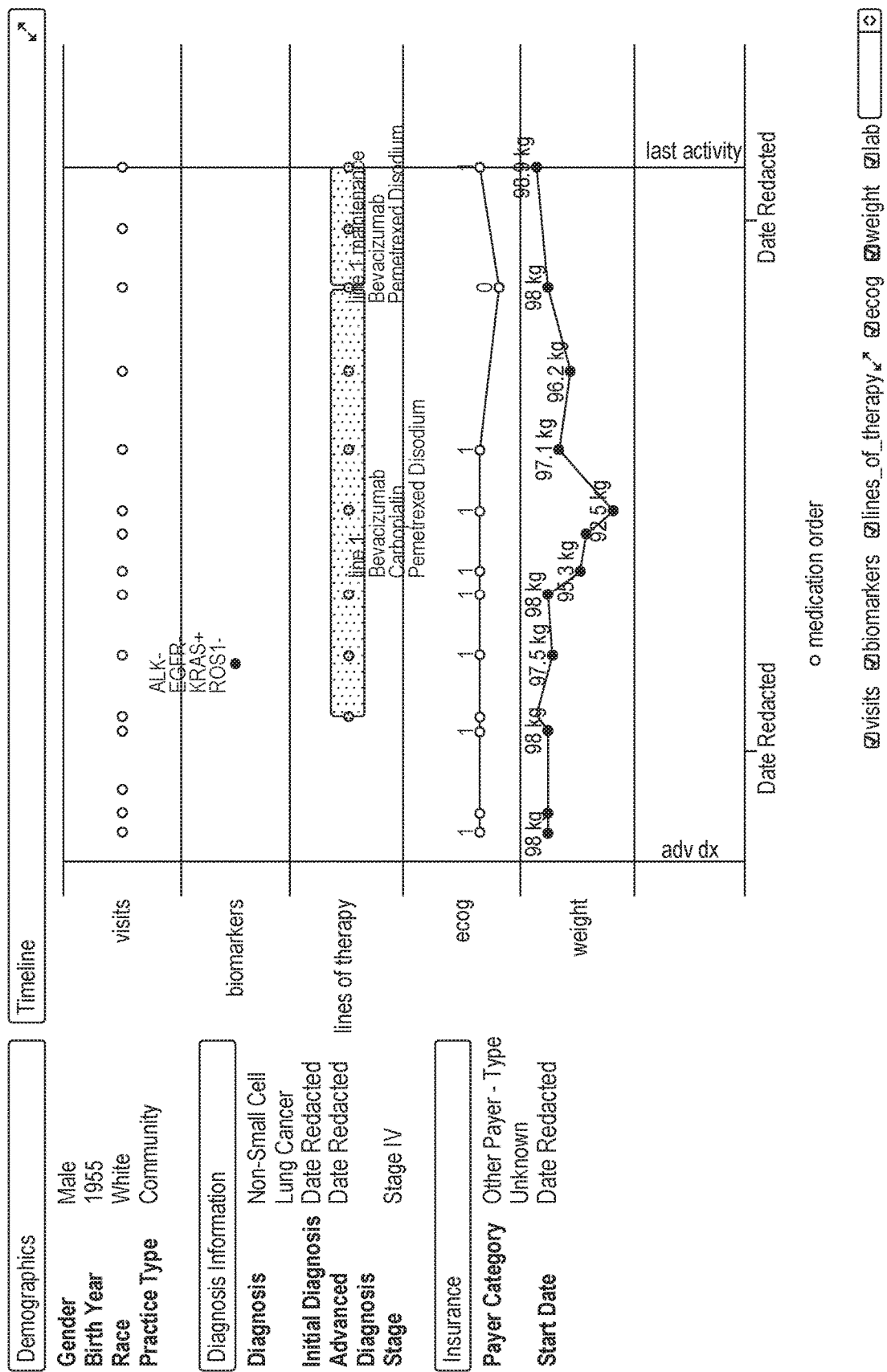
FIG. 11 is another exemplary graphical user interface, consistent with the embodiments of the present disclosure.
Figure 13:
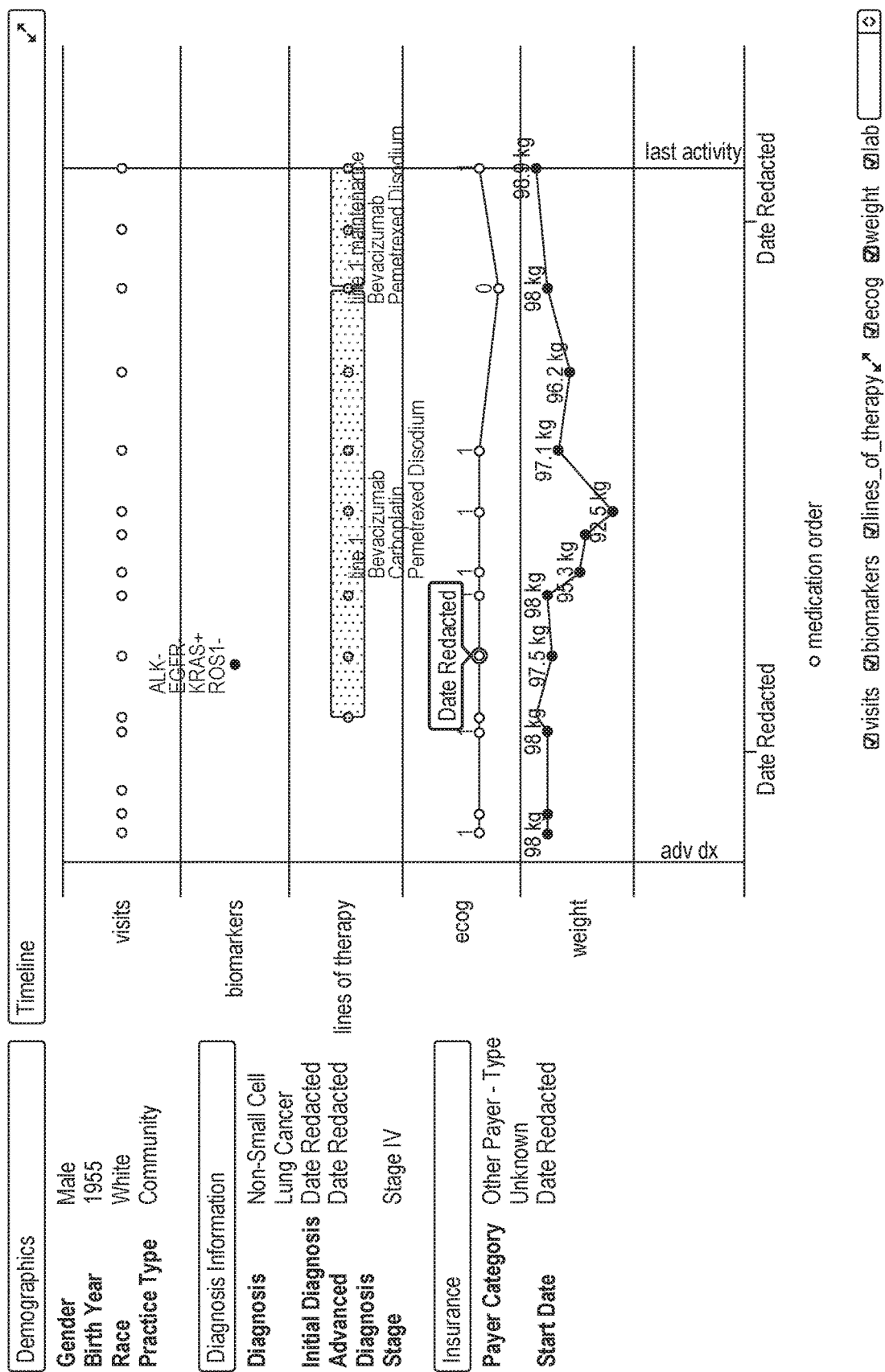
FIG. 13 is another exemplary graphical user interface, consistent with the embodiments of the present disclosure.

FIG. 9 illustrates another exemplary graphical user interface 900, consistent with embodiments of the present disclosure. User interface 900 illustrates an example of an interface or portal generated by a computing system (e.g., processing engine 110) that can be displayed on a device (e.g., client devices 140) for viewing by a user. Interface 900 can enable the user to view detailed information for a selected data point. In the exemplary embodiment of FIG. 9, interface 900 depicts detailed information for biomarkers observed on a specific date represented in the timeline. In particular, FIG. 9 shows detailed information 910 for lung cancer mutation biomarker panels ALK, EGFR, KRAS and ROS1, including status, date of specimen collection, and date result determined. In one embodiment, the detailed information is displayed in a window overlaid onto the timeline when the user selects a marker (representing a collection of a particular data point on a given date) by moving a cursor over the marker or clicking the marker. It will be readily understood from this disclosure that the number and arrangement of these elements is exemplary and that modifications can be made without departing from the teachings and embodiments consistent with the present disclosure. For example, it will be readily understood that detailed information may be displayed for other data points, such as visits, lines of therapy, ECOG score, weight, and lab results, etc.

As described above, each disease may highlight particular patient properties that are especially relevant and these highlighted properties may be displayed on the timeline, or mouse-overs can be used to provide additional information about a particular data point, such as results of a biomarker test, or each category of data displayed may be toggled on and off by a user to hone in on areas of interest, etc.

Figure 10:
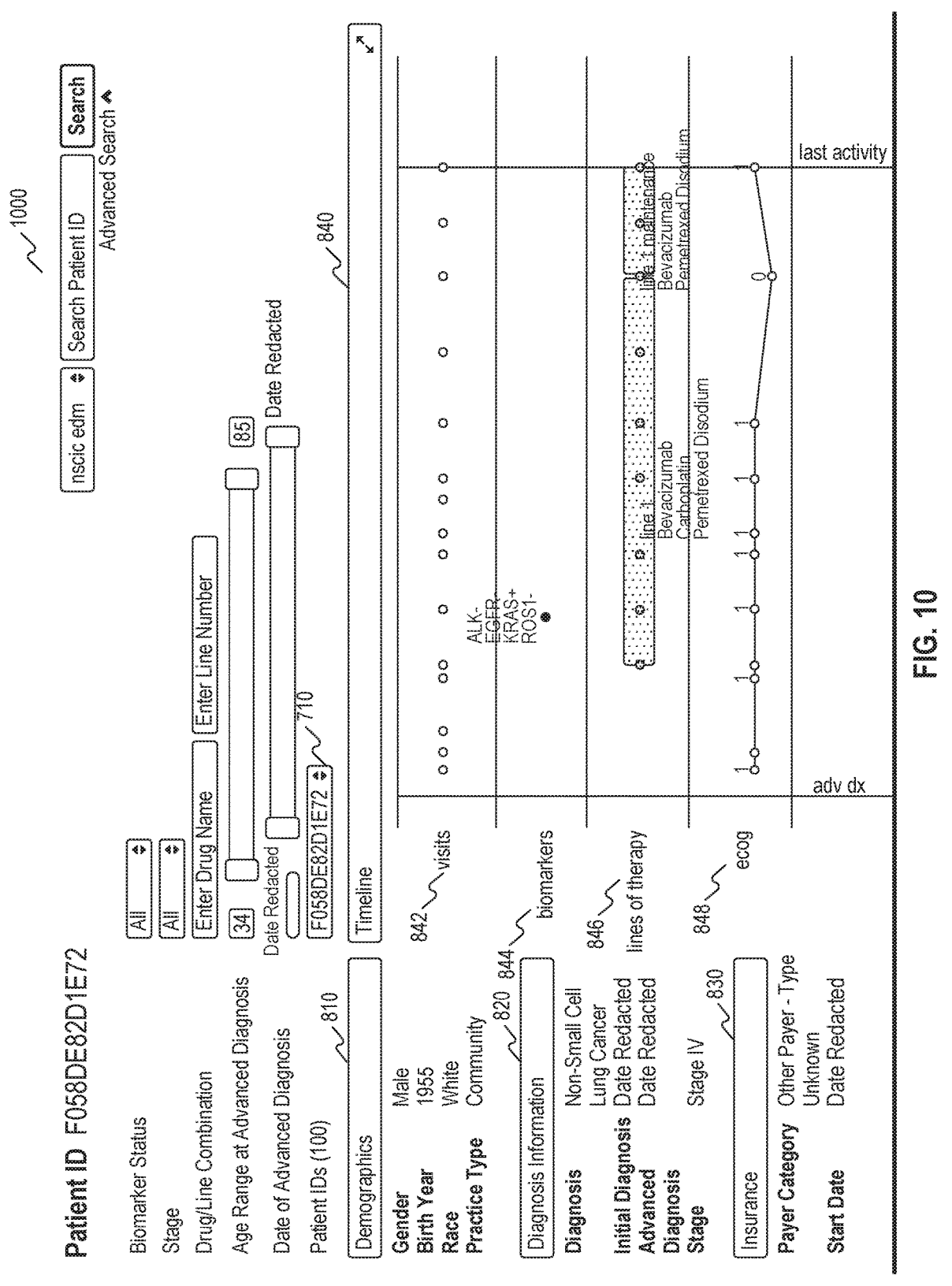

FIG. 10 illustrates another exemplary graphical user interface 1000, consistent with the embodiments of the present disclosure. User interface 1000 illustrates an example of an interface or portal generated by a computing system (e.g., processing engine 110) that can be displayed on a device (e.g., client devices 140) for viewing by a user. Interface 1000 is a hybrid of interfaces 700 and 800. As described, patient listing 710 may include patient IDs returned in response to a search performed in response to a user's selection of search button 540 or find patient button 670. In response to user selection of a patient ID, e.g., patient ID F058DE82D1E72 from patient listing 710, the user device may submit a query to a patient data system (e.g., system 105) for patient health data, e.g. demographics 810, diagnosis information 820, insurance 830 and accompanying timeline 840 with data markers for visit 842, biomarkers 844, lines of therapy 846 and ecog 848 associated with the selected patient ID, i.e., patient ID F058DE82D1E72. It will be readily understood from this disclosure that the number and arrangement of these elements is exemplary and that modifications can be made without departing from the teachings and embodiments consistent with the present disclosure.

Figure 14:
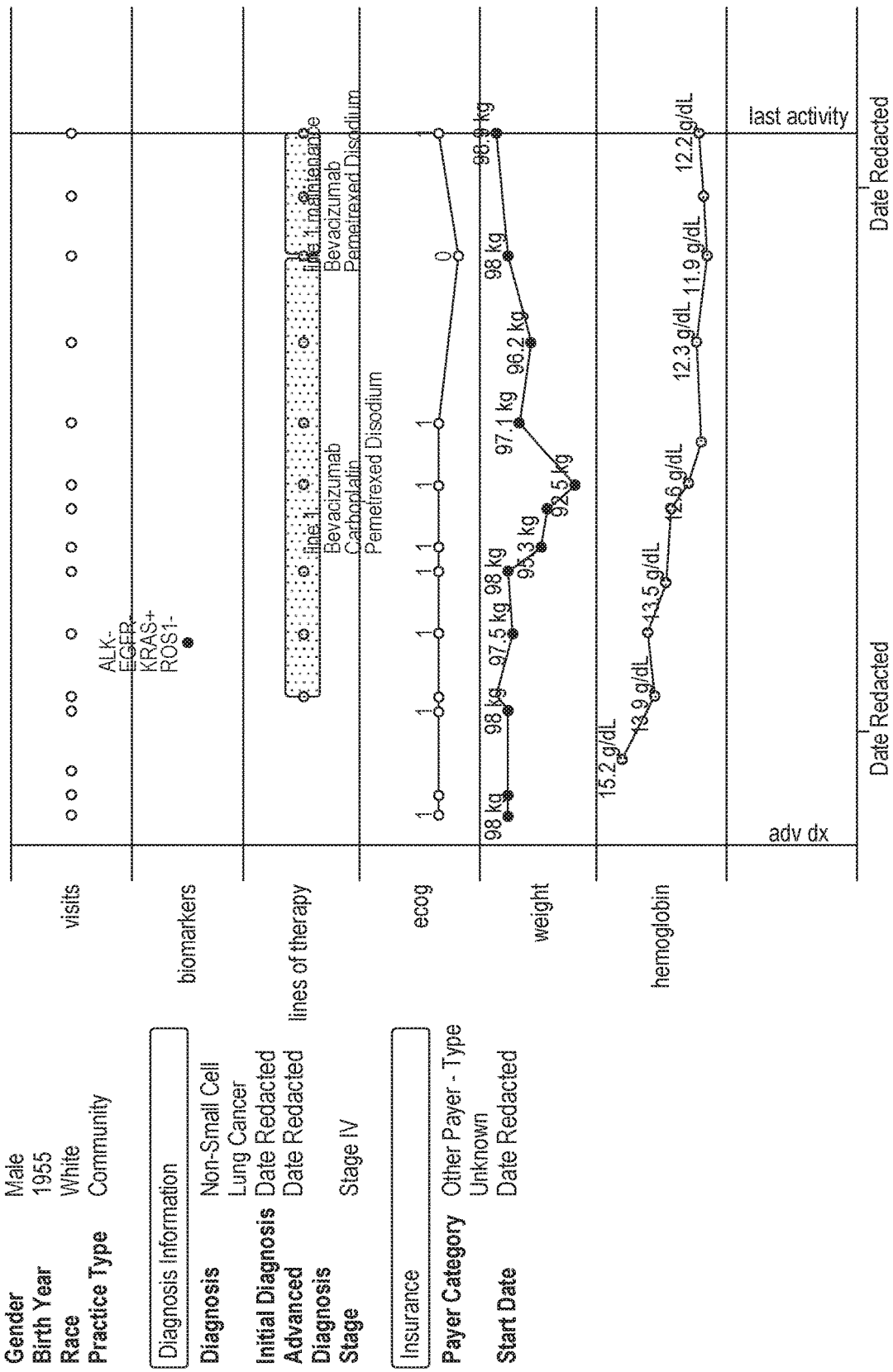
FIG. 14 is another exemplary graphical user interface, consistent with the embodiments of the present disclosure.
Figure 15:
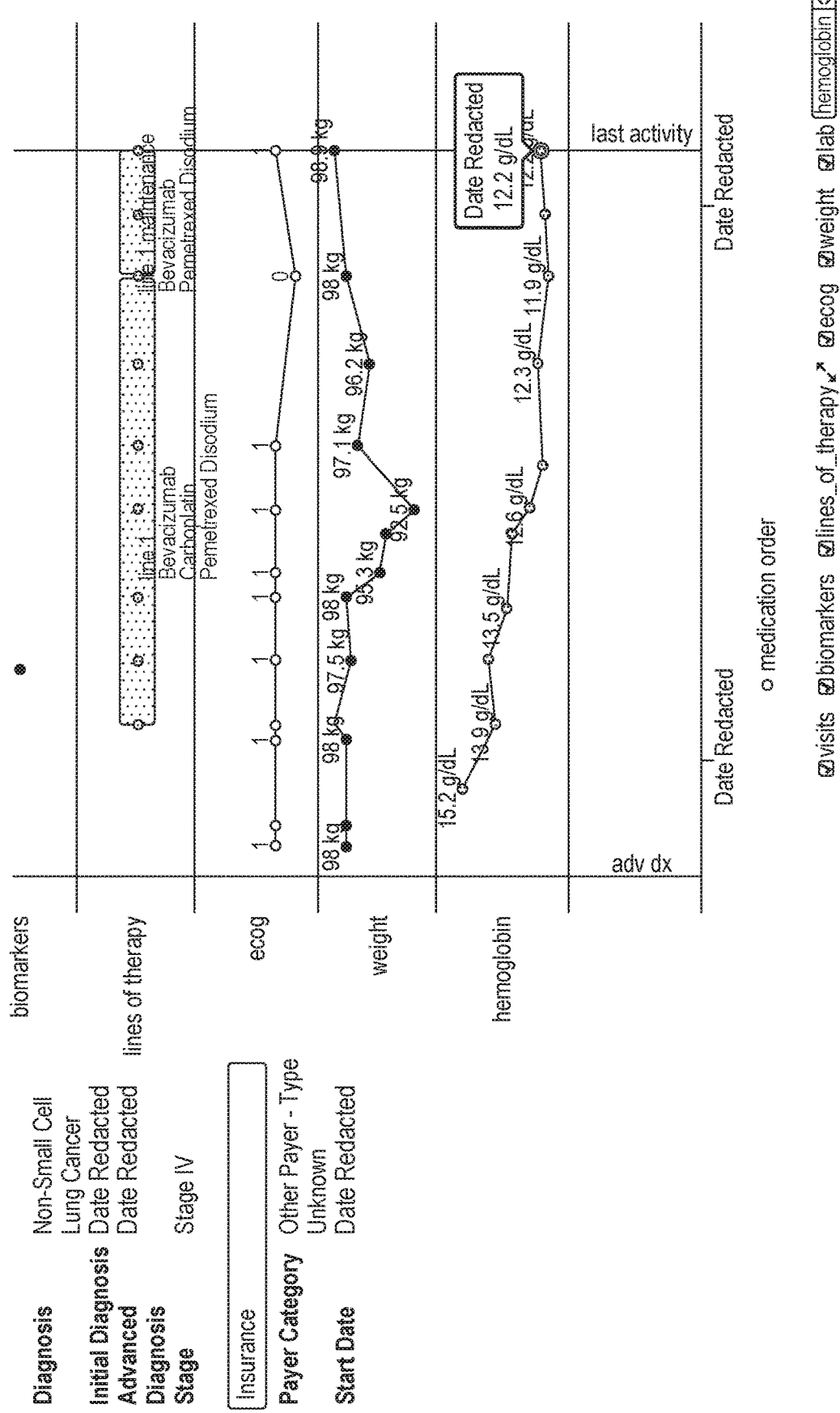
FIG. 15 is another exemplary graphical user interface, consistent with the embodiments of the present disclosure.
Figure 16:
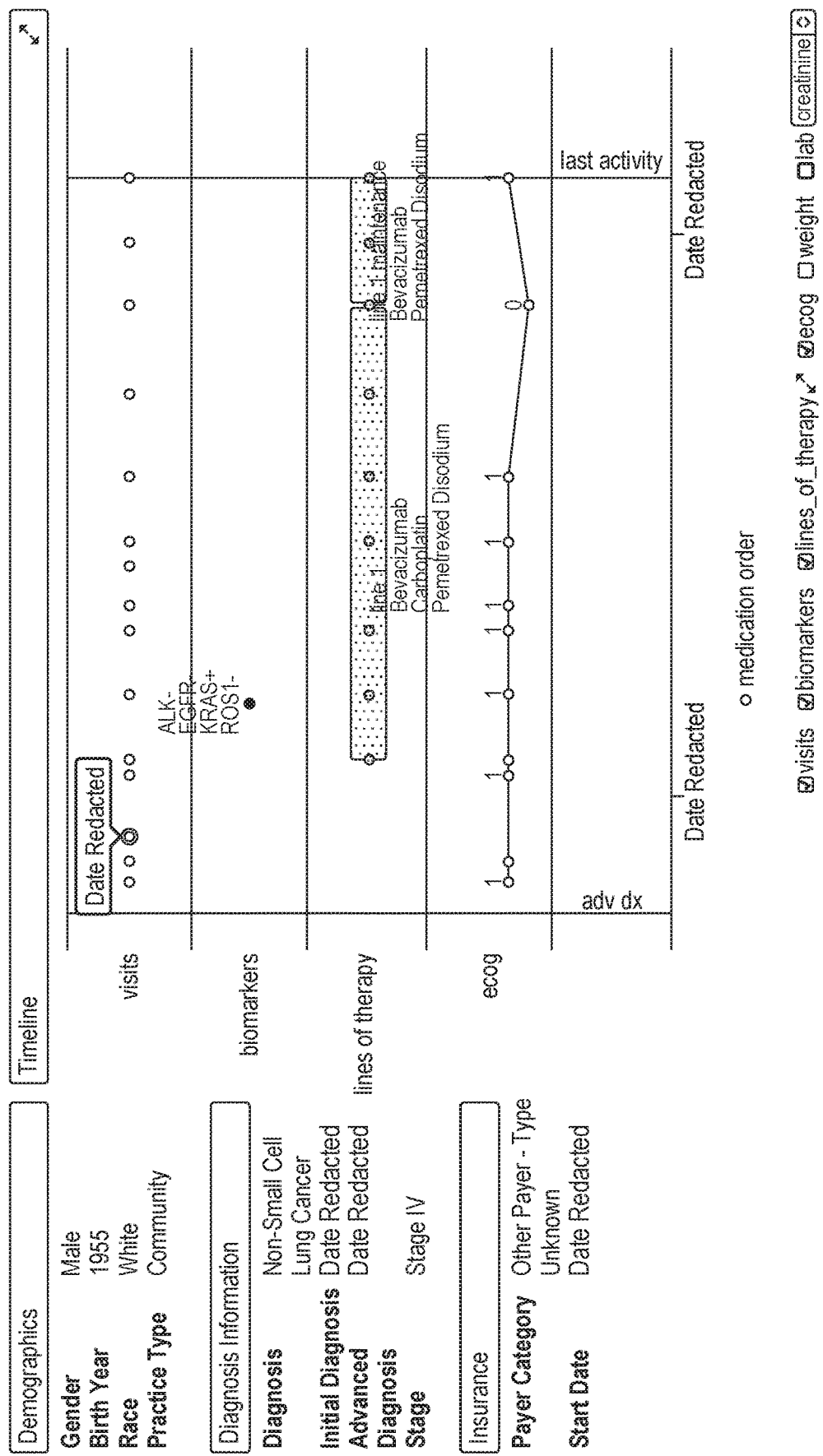
FIG. 16 is another exemplary graphical user interface, consistent with the embodiments of the present disclosure.
Figure 17:
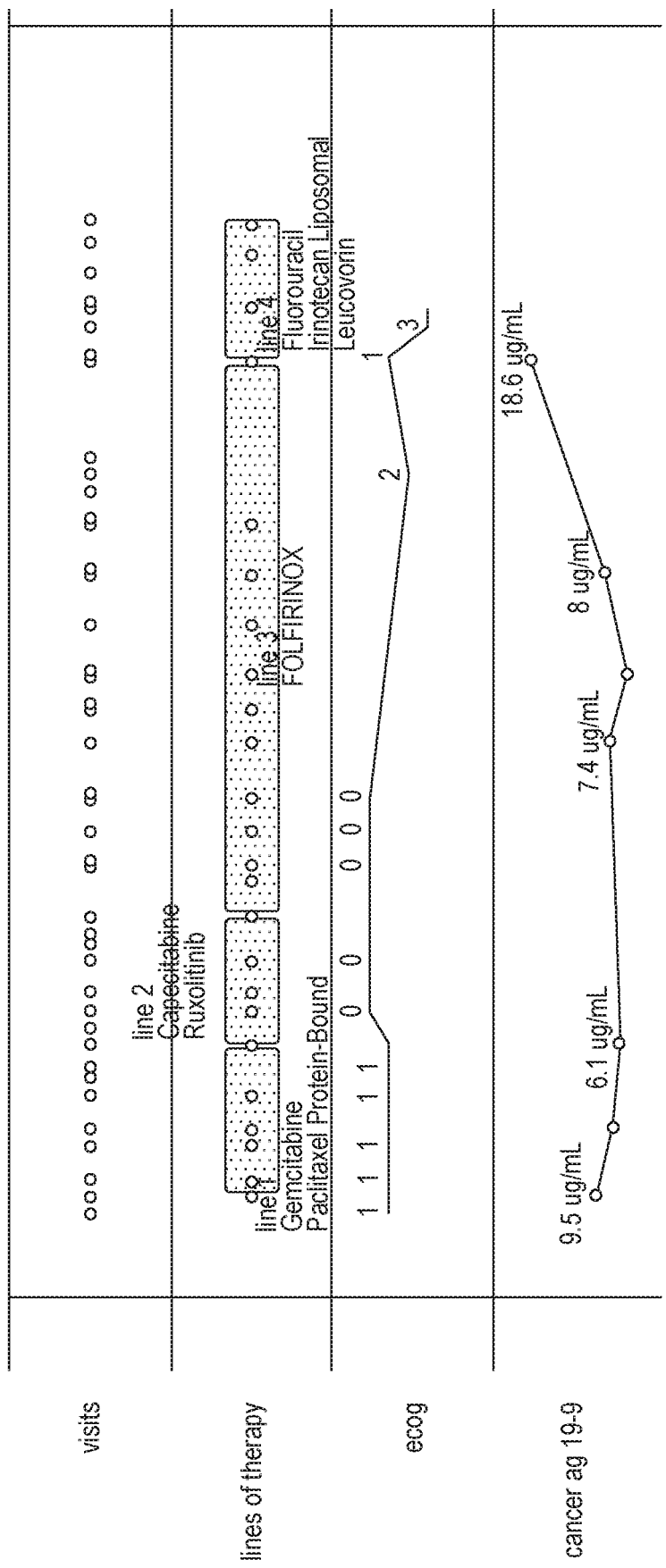
FIG. 17 is another exemplary graphical user interface, consistent with the embodiments of the present disclosure.
Figure 18:
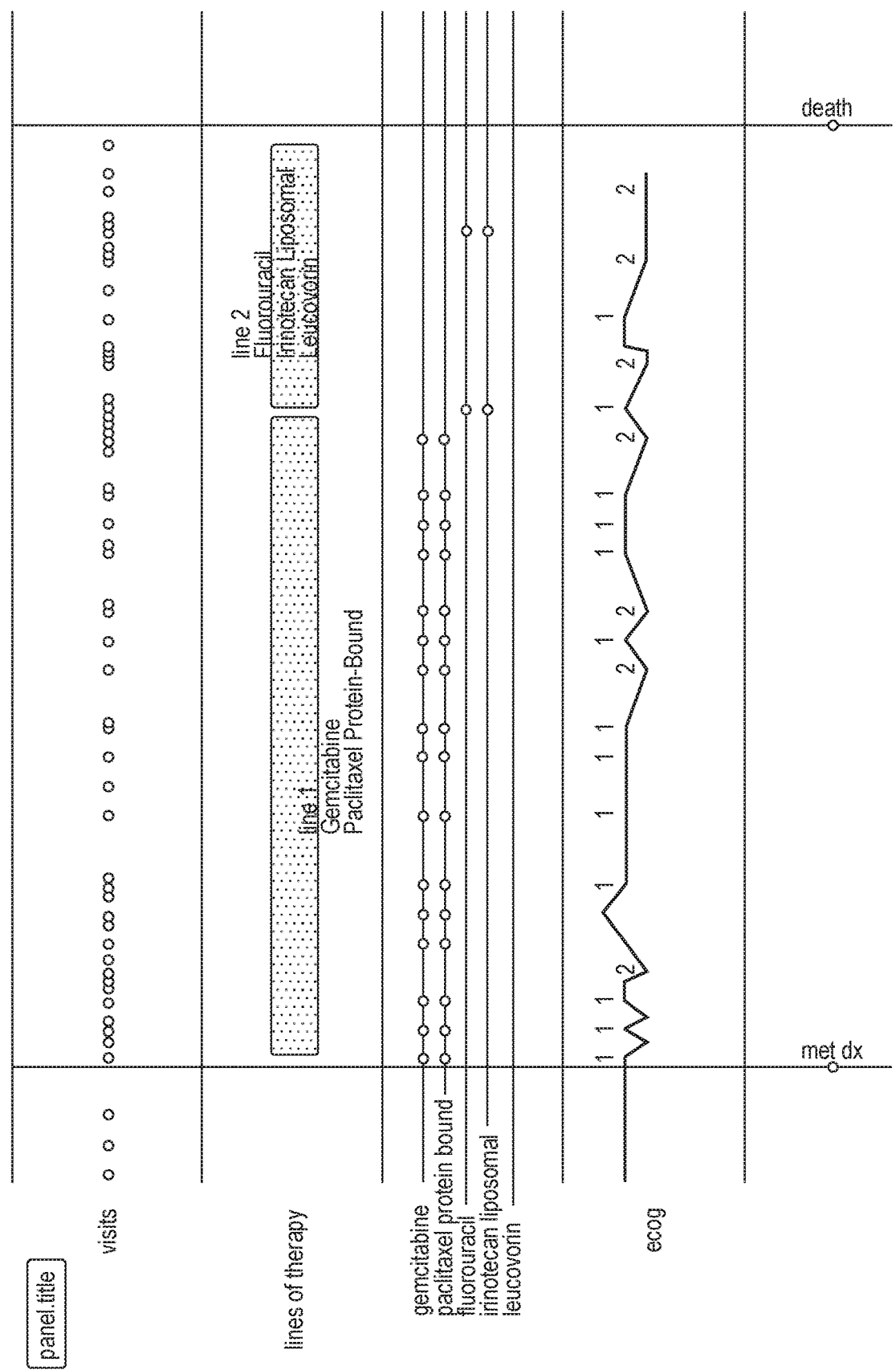
FIG. 18 is another exemplary graphical user interface, consistent with the embodiments of the present disclosure.
Figure 19:
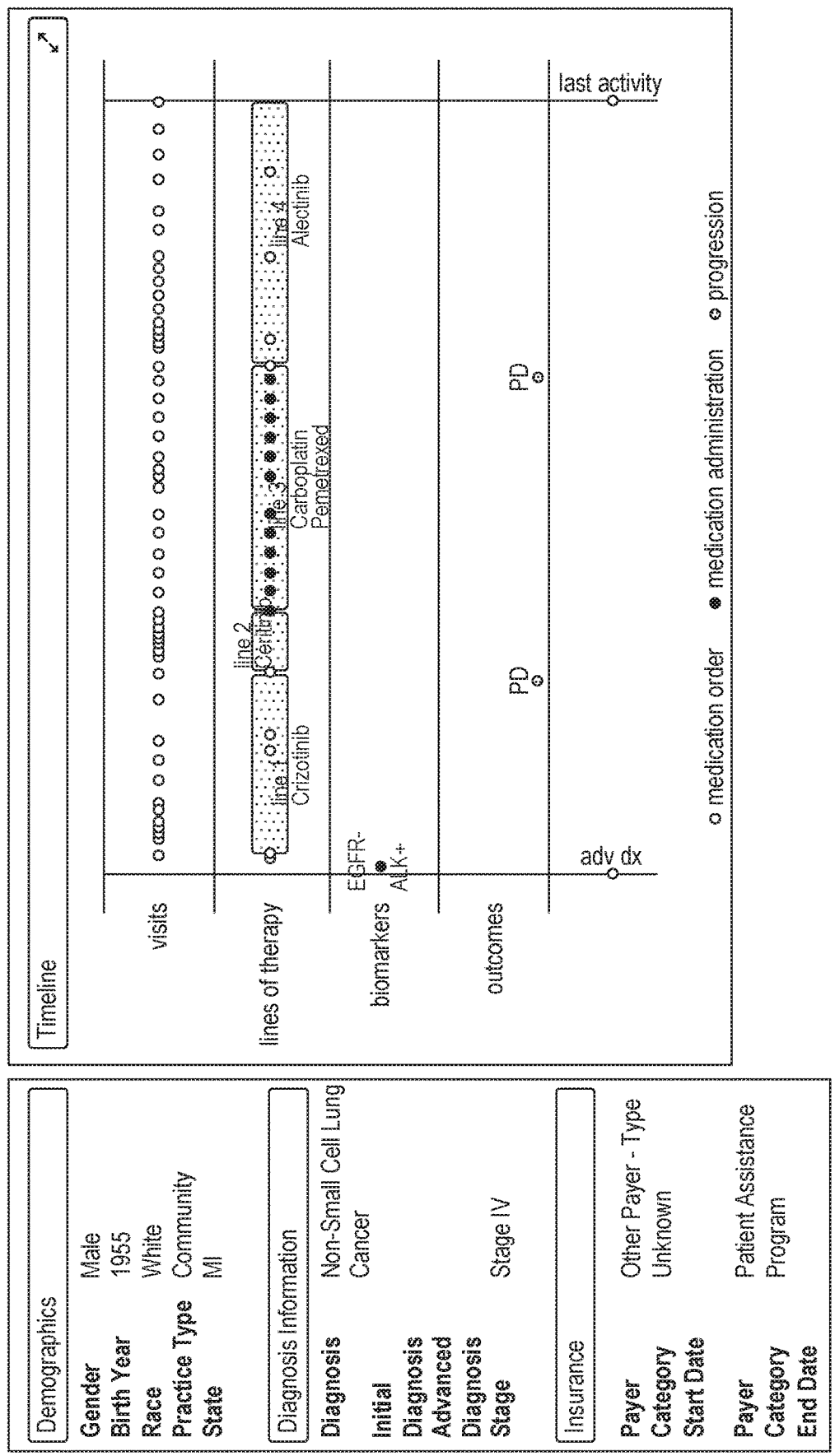
FIG. 19 is another exemplary graphical user interface, consistent with the embodiments of the present disclosure.

FIGS. 11-19 illustrate graphical user interfaces similar to the illustrations of FIGS. 8-10, consistent with embodiments of the present disclosure. For example, FIG. 14 illustrates a data event for hemoglobin levels in addition to data events for visits, biomarkers, lines of therapy, ecog and weight of a patient, while FIG. 17 illustrates a data event for cancer ag 19-9 levels in addition to data events for visits, lines of therapy and ecog for another patient.

In the preceding specification, various exemplary embodiments and features have been described with reference to the accompanying drawings. It will, however, be evident that various modifications and changes may be made thereto, and additional embodiments and features may be implemented, without departing from the broader scope of the disclosed embodiments as set forth in the claims that follow. The specification and drawings are accordingly to be regarded in an illustrative rather than restrictive sense.

For example, advantageous results still could be achieved if steps of the disclosed techniques were performed in a different order and/or if components in the disclosed systems were combined in a different manner and/or replaced or supplemented by other components. Further, the exemplary graphical user interfaces illustrated in FIGS. 5-19 are for purposes of visually understanding the teachings and embodiments of the present disclosure and are not limiting to the arrangement of the various parts of the interface, or the number of parts viewable by a user.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments.

Furthermore, while embodiments of the present disclosure have been described with reference to the processing of patient medical data, embodiments of the present disclosure may be applied to receive, process, and visualize other types of data and data in many formats, e.g., electronic data, data manually filled in paper forms, patient-reported outcomes, etc. Other implementations are also within the scope of the following exemplary claims.

Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for visualizing medical data, the system comprising:

a database;

a memory that stores a set of instructions; and at least one processor in communication with the memory and configured to execute the set of instructions to facilitate the system to:

receive the medical data in one or more formats from a plurality of sources over a network, wherein the received medical data includes unstructured medical data received from an electronic scan of patient data comprising a plurality of events associated with one or more patients;

convert the unstructured medical data from the one or more formats to a standardized structured medical data format;

store the standardized structured medical data in the database after converting the unstructured medical data;

receive a query comprising parameters received at a selector interface, the query including at least one patient characteristic;

convert the received query to a database language;

query the database with the converted query to identify, from among the one or more patients, a patient associated with the at least one patient characteristic;

generate a graphical user interface to include at least a portion of the standardized structured medical data represented as a timeline of events, wherein each of the events in the timeline corresponds to a data point in the identified patient's medical history and is represented as a first geometric shape in the generated graphical user interface;

display the generated graphical user interface;

receive a selection of an event depicted on the timeline;

generate a first window overlaid onto the timeline in response to the received selection, the first window comprising additional information associated with the selected event;

receive a patient identifier of the identified patient;

based on the patient identifier, receive line-of-therapy data including at least one line of therapy and at least one indicator of a patient response to the at least one line of therapy;

generate, in a portion of the timeline, a second geometric shape representing one or more events associated with the at least one line of therapy, the second geometric shape being different from the first geometric shape;

receive, via the graphical user interface, a user input relating to the second geometric shape; and generate, in the graphic user interface, a second window overlaid onto the timeline in response to the received user input, the second window including additional information associated with the at least one line of therapy.

2. The system of claim 1, where the at least one patient characteristic selected from a group comprising a patient identifier, a biomarker, a status, a drug and line of therapy combination, an age of patient at diagnosis, and a date of diagnosis.

3. The system of claim 1, wherein the timeline comprises a plurality of horizontal sections, each horizontal section comprises a plurality of events associated with a data point, and each of the plurality of events is associated with a date and a data point selected from a group comprising an office visit, a biomarker, a line of therapy, an ECOG score, a weight of patient and a lab result.

4. The system of claim 1, wherein the received medical data comprises structured data.

5. The system of claim 4, wherein the standardized structured medical data comprises at least one of a gender of patient, a birth year of patient, a race of patient, a visit date, a practice type, an insurance carrier, a medication order, a medication administration, an ECOG score, a weight of patient, and a lab result.

6. The system of claim 1, wherein the unstructured medical data comprises at least one of a diagnosis date, a first activity date, a stage at diagnosis, an advanced diagnosis date, a metastatic diagnosis date, a biomarker result, a tumor progression, a tumor response, and an oral medication.

7. The system of claim 1, wherein the received medical data comprises derived data, and the derived data comprises at least one of a date of death of patient, a line of therapy, and a last activity date.

8. The system of claim 1, wherein the received medical data comprises data associated with at least one line of therapy for another patient and at least one indicator of a response of the another patient to the at least one line of therapy.

9. The system of claim 1, wherein the at least one processor is further configured to execute the set of instructions to determine a modified line of therapy based on the at least one indicator of the patient response.

10. The system of claim 1, wherein the at least one processor is further configured to execute the set of instructions to facilitate the system to receive, from a user, a modification to the at least one line of therapy.

11. The system of claim 10, wherein the at least one processor is further configured to execute the set of instructions to facilitate the system to convert the modification to the at least one line of therapy to the standardized structured data format.

12. The system of claim 11, wherein the at least one processor is further configured to execute the set of instructions to facilitate the system to store the converted modification to the at least one line of therapy in the database.

13. The system of claim 11, wherein the at least one processor is further configured to execute the set of instructions to facilitate the system to modify the generated graphical user interface by adding the converted modification to the at least one line of therapy to the timeline.

14. The system of claim 1, wherein the first window comprises an inset window.

15. A computer-implemented method for visualizing medical data, the method is performed by one or more processors and comprising:

receiving the medical data in one or more formats from a plurality of sources over a network, wherein the received medical data includes unstructured medical data received from an electronic scan comprising a plurality of events associated with one or more patients;

converting the unstructured medical data from the one or more formats to a standardized structured medical data format;

storing the standardized data in a database after converting the unstructured medical data;

receiving a query comprising parameters received at a selector interface, the query including at least one patient characteristic;

converting the received query to a database language;

querying the database with the converted query to identify, from among the one or more patients, a patient associated with the at least one patient characteristic;

generating a graphical user interface to include at least a portion of the standardized structured medical data as a timeline of events, wherein each of the events in the timeline corresponding to a data point in the identified patient's medical history as is represented as a first geometric shape in the generated graphical user interface;

displaying the generated graphical user interface;

receiving a selection of an event depicted on the timeline;

generating a first window overlaid onto the timeline in response to the received selection, the first window comprising additional information associated with the selected event;

receiving a patient identifier of the identified patient;

based on the patient identifier, receiving line-of-therapy data including at least one line of therapy and at least one indicator of a patient response to the at least one line of therapy;

generating, in a portion of the timeline, a second geometric shape representing one or more events associated with the at least one line of therapy, the second geometric shape being different from the first geometric shape;

receive, via the graphical user interface, a user input relating to the second geometric shape; and generating, in the graphic user interface, a second window overlaid onto the timeline in response to the received user input, the second window including additional information associated with the at least one line of therapy.

16. The method of claim 15, wherein the at least one patient characteristic selected from a group comprising patient ID, biomarker, status, drug and line of therapy combination, age of patient at diagnosis and date of diagnosis.

17. The method of claim 15, wherein the timeline comprising a plurality of horizontal sections, and wherein each horizontal section comprising a plurality of events associated with a data point selected from a group comprising office visit, biomarker, line of therapy, ECOG score, weight of patient and lab results.

18. The method of claim 15, wherein the received medical data comprises structured data.

19. A non-transitory computer-readable storage medium comprising a set of instructions executable by at least one processor to perform a method for visualizing medical data, the method comprising:
- receiving the medical data in one or more formats from a plurality of sources over a network, the medical data comprising a plurality of events associated with one or more patients, and wherein the received medical data comprising unstructured data received from an electronic scan of the plurality of events associated with the one or more patients;
- converting the unstructured medical data from the one or more formats to a standardized structured medical data format;
- storing the standardized structured medical data in a database after converting the unstructured medical data;
- receiving a query comprising parameters received at a selector interface, the query including at least one patient characteristic selected from a group comprising a patient identifier, a biomarker, a status, a drug and line of therapy combination, an age of patient at diagnosis, and a date of diagnosis;
- converting the received query to a database language;
- querying the database with the converted query to identify, from among the one or more patients, a patient associated with the at least one patient characteristic;
- generating a graphical user interface including a timeline of events, wherein each of the events in the timeline corresponding to a data point in the identified patient's medical history and is represented as a first geometric shape in the generated graphical user interface;
- displaying the generated graphical user interface;
- receiving a selection of an event depicted on the timeline;
- generating a first window overlaid onto the timeline in response to the received selection, the first window comprising additional information associated with the selected event;
- receiving a patient identifier of the identified patient;
- based on the patient identifier, receiving line-of-therapy data including at least one line of therapy and at least one indicator of a patient response to the at least one line of therapy;
- generating, in a portion of the timeline, a second geometric shape representing one or more events associated with the at least one line of therapy, the second geometric shape being different from the first geometric shape;
- receive, via the graphical user interface, a user input relating to the second geometric shape; and
- generating, in the graphic user interface, a second window overlaid onto the timeline in response to the received user input, the second window including additional information associated with the at least one line of therapy.

20. A system for visualizing medical data, the system comprising:
- a database;
- one or more data sources;
- one or more client devices; and
- an apparatus communicatively connected to the database, data sources and client devices over a network, wherein the apparatus comprising a memory to store a set of instructions and one or more processors in communication with the memory and configured to execute the set of instructions to cause the apparatus to:
  - receive, from the one or more data sources, the medical data in one or more formats, the medical data comprising a plurality of events associated with one or more patients, and wherein the received medical data comprises structured data and unstructured data received from an electronic scan of the plurality of events associated with the one or more patients;
  - convert the unstructured medical data from the one or more formats to a standardized structured medical data format;
  - store the standardized structured medical data in the database after converting the unstructured medical data;
  - receive a query comprising parameters received at a selector interface, the query including at least one patient characteristic selected from a group comprising a patient identifier, a biomarker, status, a drug and line of therapy combination, an age of the patient at diagnosis, and a date of the diagnosis;
  - convert the received query to a database language;
  - query the database with the converted query to identify, from among the one or more patients, a patient associated with the at least one patient characteristic;
  - generate a graphical user interface to include at least a portion of the standardized structured medical data as a timeline of events for the one or more patients, wherein each of the events in the timeline corresponds to a data point in a respective patient's medical history and is represented as a first geometric shape in the generated user interface;
  - display the generated graphical user interface;
  - receive a selection of an event depicted on the timeline;
  - generate a first window overlaid onto the timeline in response to the received selection, the first window comprising additional information associated with the selected event;
  - receive a patient identifier of the identified patient;
  - based on the patient identifier, receive line-of-therapy data including at least one line of therapy and at least one indicator of a patient response to the at least one line of therapy;
  - generate, in a portion of the timeline, a second geometric shape representing one or more events associated with the at least one line of therapy, the second geometric shape being different from the first geometric shape;
  - receive, via the graphical user interface, a user input relating to the second geometric shape; and
  - generate, in the graphic user interface, a second window overlaid onto the timeline in response to the received user input, the second window including additional information associated with the at least one line of therapy.

* * * * *

UNITED STATES PATENT AND TRADEMARK OFFICE
CERTIFICATE OF CORRECTION

PATENT NO. : 11,133,094 B2
APPLICATION NO. : 15/717677
DATED : September 28, 2021
INVENTOR(S) : Melisa Tucker et al.

Page 1 of 1

It is certified that error appears in the above-identified patent and that said Letters Patent is hereby corrected as shown below:

In the Claims

In Claim 17, Column 18, Line 61, "comprising" should read as --comprises--.

In Claim 17, Column 18, Line 62, "comprising" should read as --comprises--.

In Claim 19, Column 19, Line 9, "comprising" should read as --comprises--.

In Claim 19, Column 19, Line 30, "corresponding" should read as --corresponds--.

Signed and Sealed this
Twenty-first Day of November, 2023

Katherine Kelly Vidal
*Director of the United States Patent and Trademark Office*